US012702643B2

(12) United States Patent
Nielsen

(10) Patent No.: US 12,702,643 B2
(45) Date of Patent: Aug. 11, 2026

(54) ION-EXCHANGE COMPOSITION WITH WATER-SOLUBLE MUCOADHESIVE POLYMERS

(71) Applicant: Fertin Pharma A/S, Vejle (DK)

(72) Inventor: Kent Albin Nielsen, Brande (DK)

(73) Assignee: Fertin Pharma A/S, Vejle (DK)

( * ) Notice: Subject to any disclaimer, the term of this patent is extended or adjusted under 35 U.S.C. 154(b) by 87 days.

(21) Appl. No.: 16/599,991

(22) Filed: Oct. 11, 2019

(65) Prior Publication Data

US 2021/0106516 A1 Apr. 15, 2021

(51) Int. Cl.

*A61K 9/00* (2006.01)
*A61K 9/20* (2006.01)
*A61K 31/465* (2006.01)

(52) U.S. Cl.

CPC ............ *A61K 9/006* (2013.01); *A61K 9/0056* (2013.01); *A61K 9/2018* (2013.01); *A61K 9/2027* (2013.01); *A61K 31/465* (2013.01)

(58) Field of Classification Search

CPC .. A61K 2300/00; A61K 47/26; A61K 9/0043; A61K 9/0048; A61K 31/185; A61K 31/385; A61K 31/70; A61K 31/4439; A61K 31/485; A61K 31/137; A61K 31/7016; A61K 9/006; A61K 31/138; A61K 9/2054; A61K 47/38; A61K 9/0056; A61K 31/135; A61K 45/06; A61K 31/166; A61K 47/22; A61K 47/32; A61K 9/2027; A61K 31/15; A61K 31/164; A61K 31/165; A61K 31/343; A61K 31/381; A61K 31/4515; A61K 31/4525; A61K 31/454; A61K 31/496; A61K 31/519; A61K 31/5377; A61K 31/5415; A61K 31/55; A61K 31/551; A61K 31/553; A61K 31/554; A61K 9/0065;

(Continued)

(56) References Cited

U.S. PATENT DOCUMENTS 6,368,625 B1 * 4/2002 Siebert ................ A61K 9/0056 424/466
8,846,075 B2 9/2014 Jonsson et al.

(Continued)

FOREIGN PATENT DOCUMENTS

EP 1578422 B1 4/2007
EP 2233134 A1 9/2010

(Continued)

OTHER PUBLICATIONS

ISR and Written Opinion of the ISA dated Jan. 28, 2021 in PCT/DK2020/050280.

(Continued)

*Primary Examiner* — Isis A Ghali
*Assistant Examiner* — Ayaan A Alam
(74) *Attorney, Agent, or Firm* — Harris Beach Murtha Cullina PLLC

(57) ABSTRACT

The present invention relates to an oral tablet for oromucosal delivery of biologically active compounds, the tablet comprising a sugar alcohol composition comprising one or more sugar alcohol particles in an amount of at least 20% by weight of the tablet, an ion-exchange composition comprising a plurality of particles of at least one water-soluble anionic mucoadhesive polymer loaded with a cationic biologically active compound.

18 Claims, 1 Drawing Sheet

| Precipitate | T0 | T-5min | T-10min | + H2O |
| --- | --- | --- | --- | --- |
| G(IPA) | | | | |
| G | | | | |

(58) Field of Classification Search

CPC ...... A61K 9/08; A61K 9/2018; A61K 9/2095; A61K 38/12; A61K 38/29; A61K 38/28; A61K 31/196; A61K 31/395; A61K 31/4468; A61K 31/4545; A61K 31/495; A61K 31/522; A61K 38/26; A61K 9/0053; A61K 9/19; A61K 31/7012; A61K 31/44; A61K 31/465; A61K 31/517; A61K 31/722; A61K 38/00; A61K 38/2264; A61K 38/2278; A61K 47/02; A61K 47/12; A61K 47/183; A61K 47/585; A61K 47/60; A61K 47/61; A61K 47/6953; A61K 9/0019; A61K 9/0073; A61K 9/1611; A61K 9/1652; A61K 9/20; A61K 9/2063; A61K 9/2072; A61K 9/2077

See application file for complete search history.

(56) References Cited

U.S. PATENT DOCUMENTS

| | | | | |
|---|---|---|---|---|
| 9,161,908 | B2 | 10/2015 | Nilsson | |
| 9,925,145 | B2 | 3/2018 | Hubinette et al. | |
| 2005/0196440 | A1* | 9/2005 | Masters | A61K 38/38 424/464 |
| 2006/0039872 | A1* | 2/2006 | Schmidt | A23G 4/20 424/48 |
| 2011/0300224 | A1* | 12/2011 | Murpani | A61P 43/00 424/495 |
| 2012/0039981 | A1* | 2/2012 | Pedersen | A61K 9/0058 424/440 |
| 2014/0230833 | A1* | 8/2014 | Andersen | A24B 15/10 131/270 |
| 2015/0020818 | A1 | 1/2015 | Gao et al. | |
| 2017/0172995 | A1 | 6/2017 | Repaka et al. | |
| 2018/0140554 | A1* | 5/2018 | Wittorff | A61K 9/2086 |
| 2019/0124971 | A1 | 5/2019 | Soffe et al. | |
| 2019/0350847 | A1* | 11/2019 | Wittorff | A61Q 11/00 |

FOREIGN PATENT DOCUMENTS

| | | | | |
|---|---|---|---|---|
| WO | 9742941 | | 11/1997 | |
| WO | 2004075877 | A1 | 9/2004 | |
| WO | WO-2009007768 | A1 * | 1/2009 | A23G 3/004 |
| WO | 2009134947 | A1 | 11/2009 | |
| WO | 2010114445 | A1 | 10/2010 | |
| WO | 2012083947 | A1 | 6/2012 | |
| WO | 2013147687 | A1 | 10/2013 | |
| WO | 2018091048 | A1 | 5/2018 | |
| WO | 2018113916 | | 6/2018 | |
| WO | 2021004928 | A1 | 1/2021 | |

OTHER PUBLICATIONS

Park, C.R. and Munday, D.L., Development and evaluation of a biphasic buccal adhesive tablet for nicotime replacement therapy, International Journal of Pharmaceutics 237 (2002) 215-226.

* cited by examiner

| Precipitate | T0 | T-5min | T-10min | + H2O |
|---|---|---|---|---|
| G(IPA) | | | | |
| G | | | | |

ION-EXCHANGE COMPOSITION WITH WATER-SOLUBLE MUCOADHESIVE POLYMERS

FIELD OF THE INVENTION

The present invention relates to the field of ion-exchange compositions for loading of cationic biologically active compounds. In particular, the invention relates to ion-exchange compositions based on particles of water-soluble anionic mucoadhesive polymers.

BACKGROUND OF THE INVENTION

Ion-exchange resins have traditionally been used in the field of oral delivery in order to obtain controlled release and delivery of biologically active compounds, such as nicotine. The aim with ion-exchange resins has been to stabilize the biologically active compound and at the same time secure a controlled release of the biologically active compounds, such as nicotine, upon oral administration. Adverse effects of the biologically active compounds, such as throat irritation, may in this way be alleviated, while the biologically active compounds may be delivered over an extended period of time for increased craving relief to a user in need thereof.

Nicotine is a well known, highly characterized alkaloid that can be isolated from the dried leaves of *Nicotiana tabacum*. Its numerous commercial uses include utilities such as a fumigant, an insecticide and the like. It is of therapeutically valuable in the treatment of the smoking withdrawal syndrome. This treatment is based on the fact that the administration of nicotine into the body has been readily accomplished by the method of smoking, e.g. from cigarettes, pipes or cigars. The smoker experiences a satisfactory sensation from such administration.

U.S. Pat. No. 3,901,248 discloses a chewable smoking substitute composition which comprises a chewing gum base and a nicotine/cation exchange resin complex dispersed in said chewing gum. When such composition is chewed, nicotine is released in small and reduced amounts into the mouth, within the first few minutes of chewing. The composition is marginally effective in inducing the pleasurable sensation of smoking that is typically desired from those engaged in the therapy that incorporates such chewing gum. However, although the composition may generally result in less adverse effects, such as throat irritation, a waste amount of nicotine is swallowed by the user due to the extended release properties and hence bioavailability of the nicotine present in the formulation may be relatively low.

While the prior art ion-exchange resins generally comply with stability requirements and have been used in nicotine products for decades, there is still a need in the art for ion-exchange compositions suitable for use in oromucosal delivery of biologically active compounds without the drawbacks of the prior art. Particularly, there is a need in the art for ion-exchange compositions that provide improved bioavailability of biologically active compounds, such as nicotine.

SUMMARY OF THE INVENTION

The present invention pertains to an oral tablet for oromucosal delivery of biologically active compounds, the tablet comprising a sugar alcohol composition comprising one or more sugar alcohol particles in an amount of at least 20% by weight of the tablet, an ion-exchange composition comprising a plurality of particles of at least one water-soluble anionic mucoadhesive polymer loaded with a cationic biologically active compound.

Generally, the ion-exchange composition of the present invention unlike traditional ion-exchange resins is associated with mucoadhesive properties. Hence, when the ion-exchange composition of the present invention is administered, the ion-exchange composition tends to adhere to mucosal surfaces where the biologically active compounds may be delivered directly to the oral mucosa and absorbed into the bloodstream. This characteristic of the ion-exchange composition may address various of the challenges of the prior art.

One of the challenges that may be solved according to the invention is improved bioavailability of biologically active compounds, i.e. the content of biologically active compounds in the oral formulation that is made available for transport through the oral mucosa. In other words, the invention serves to solve the challenges of maximizing the usability of the active compounds available for uptake and avoids that too much of the biologically active compounds is swallowed during use.

Consequently, by maximizing the usage of the biologically active compounds, certain side-effects of the biologically active compounds may be avoided. For instance, the adverse effect of nicotine may be avoided or at least alleviated. Swallowing high amounts of nicotine is known to result in throat irritation and discomfort to the user. Hence, by optimizing the bioavailability of the biologically active compounds, adverse side effects may be improved according to the invention.

Another consequence of the present invention is that a higher content of biologically active compounds may be used in the oral formulation as a result of less pronounced adverse side effects. In the same context, this also gives an option of formulating with a lower content of biologically active compounds and at the same time obtaining the same or similar pharmacological effects of the biologically active compounds due to a higher bioavailability.

Importantly, the ion-exchange composition of the present invention comprises a plurality of particles wherein the biologically active compounds may be protected until they adhere to the mucosal surface where they are delivered directly to the oral mucosa and absorbed into the bloodstream. At least two benefits are associated with this route of targeting the biologically active compounds as part of particles to the site of action. Firstly, less waste of the biologically active compounds may be achieved. Secondly, higher bioavailability may be achieved. In this connection, it was observed that administering water-soluble anionic mucoadhesive polymers without formulating these into particles according to the invention had the result of less bioavailability and a higher degree of adverse effects.

Surprisingly, it was seen that pronounced adherence of the particles of the at least one water-soluble anionic mucoadhesive polymer according to the invention was associated with a higher concentration of the biologically active compounds in discrete areas of the oral mucosa. Hence, when the particles of the invention adhered to the oral mucosa, the local concentration of the biologically active compound was increased considerably. Without being bound by theory, this local high concentration of biologically active compounds is believed to result in a higher uptake of the biologically active compounds, such as nicotine.

In context of the advantages of an upconcentration of the biologically active compounds on the oral mucosa and protection offered by the particles both before they adhere to the oral mucosa and while they are adhered to the oral mucosa, the present invention may also serves to increase the overall uptake of nicotine compared to conventional oral formulations with the same content of biologically active ingredients. Also, in this context, the present invention may offer less side effects associated with swallowing the biologically active compounds.

According to the invention, the oral formulation is preferably designed for the ion-exchange composition to reach the oral mucosa within a certain time. This accommodates adherence to the oral mucosa and exposes the ion-exchange composition to a minimum amount of saliva. Hence, the ion-exchange composition is preferably formulated in an oral tablet with a certain amount of sugar alcohol present that contributes to disintegration of the tablet and thereby releases the ion-exchange composition after a relatively short time. Such tablets may include fast disintegrating tablets (FDT) or orally disintegrating tablets (ODT), certain chewable tablets, powder as such and sachets.

Typically, traditional lozenges would not provide the required disintegration that allows the ion-exchange composition to reach the oral mucosa within a short period of time. However, in certain embodiments the ion-exchange composition of the present invention may be formulated into lozenges and even into the water-insoluble part of a chewing gum. In these embodiments, the ion-exchange composition works in a similar manner as ion-exchange resins and are partly retained in the formulation matrix for an extended period of time. Followingly, the biologically active compounds are released over an extended period of time. Nevertheless, in contrast to ion-exchange resins, the anionic mucoadhesive polymer is partly dissolved over time due to the water-soluble nature of the polymer, which is considered a clear benefit with respect to bioavailability of the biologically active compounds.

The ion-exchange composition according to the invention comprises a plurality of particles of at least one water-soluble anionic mucoadhesive polymer loaded with a cationic biologically active compound. The ion-exchange composition as such may comprise additional components or ingredients apart from the at least one water-soluble anionic mucoadhesive polymer loaded with a cationic biologically active compound, such as a buffering agent.

Also, the at least one water-soluble anionic mucoadhesive polymer is loaded with a cationic biologically active compound, such as nicotine. The ion-exchange composition serves to provide a stable composition upon storage as such and when formulated in oral tablets with additional ingredients. Additionally, the ion-bonding properties work in a similar way compared to traditional cation exchange resins. Release of the biologically active compounds is for instance accommodated with the right pH conditions, while in other pH conditions, the complex may be stable. The at least one water-soluble anionic mucoadhesive polymer has a similar function as for instance a polacrilex resin used for loading nicotine, i.e. a porous structure.

Traditional ion-exchange resins are polymers that contain appropriately substituted acidic groups, such as carboxylic and sulfonic for cation exchangers; or basic groups, such as quaternary ammonium group for anion exchangers. Variables relating to the resin are the exchange capacity; degree of cross-linking, which determines the permeability of the resin, its swelling potential, and the access of the exchange sites to the drug ion; the effective pK(a) of the exchanging group, which determines the exchange affinity; and the resin particle size, which controls accessibility to the exchange ions.

Contrary to traditional resins, the at least one water-soluble anionic mucoadhesive polymers of the present invention are water-soluble. However, the polymers of the present invention are generally associated with similar side group substitution capacities, acid properties, swelling properties, access of the exchange site to the drug ion, effective pK(a) of the exchanging group as well as particle sizes.

In one embodiment of the invention, the weight ratio of the at least one water-soluble anionic mucoadhesive polymer to the cationic biologically active compound is from 2:1 to 20:1.

In one embodiment of the invention, the weight ratio of the at least one water-soluble anionic mucoadhesive polymer to the cationic biologically active compound is from 2:1 to 15:1.

In one embodiment of the invention, the weight ratio of the at least one water-soluble anionic mucoadhesive polymer to the cationic biologically active compound is from 2:1 to 10:1.

In one embodiment of the invention, the weight ratio of the at least one water-soluble anionic mucoadhesive polymer to the cationic biologically active compound is from 3:1 to 8:1.

In one embodiment of the invention, the cationic biologically active compound comprises an amine functional group.

In one embodiment of the invention, the cationic biologically active compound is nicotine.

In certain other embodiments of the invention, the cationic biologically active compound is selected from the group consisting of bisphosphonates, captopril, furosemide, metformin, gabapentin, levodopa, baclofen, ciprofloxacin, tannin, proclorperazine, tramadol, salbutamol, furosemide, piribedil, irinotecan, zolmitriptan, clonidine, amphotericin B, cetylpyridinium, ritodrine, pregabalin and zaleplon.

The presently most preferred cationic biologically active compound is selected from the group consisting of metformin, salbutamol and cetylpyridinium. In one embodiment of the invention, the cationic biologically active compound is metformine. In one embodiment of the invention, the cationic biologically active compound is salbutamol. In one embodiment of the invention, the cationic biologically active compound is cetylpyridinium.

In one embodiment of the invention, average particle diameter of the plurality of particles of the at least one water-soluble anionic mucoadhesive polymer is from 10 to 2000 microns.

In one embodiment of the invention, the average particle diameter of the plurality of particles of the at least one water-soluble anionic mucoadhesive polymer is from 10 to 1000 microns.

In one embodiment of the invention, the average particle diameter of the plurality of particles of the at least one water-soluble anionic mucoadhesive polymer is from 20 to 500 microns.

In certain other embodiments of the invention, the average particle diameter of the plurality of particles of the at least one water-soluble anionic mucoadhesive polymer is from 10 to 800 microns. In certain other embodiments of the invention, the average particle diameter of the plurality of particles of the at least one water-soluble anionic mucoadhesive polymer is from 10 to 700 microns. In certain other embodiments of the invention, the average particle diameter of the plurality of particles of the at least one water-soluble anionic mucoadhesive polymer is from 10 to 600 microns. In certain other embodiments of the invention, the average particle diameter of the plurality of particles of the at least one water-soluble anionic mucoadhesive polymer is from 10 to 500 microns. In certain other embodiments of the invention, the average particle diameter of the plurality of particles of the at least one water-soluble anionic mucoadhesive polymer is from 20 to 400 microns. In certain other embodiments of the invention, the average particle diameter of the plurality of particles of the at least one water-soluble anionic mucoadhesive polymer is from 20 to 400 microns. In certain other embodiments of the invention, the average particle diameter of the plurality of particles of the at least one water-soluble anionic mucoadhesive polymer is from 30 to 400 microns. In certain other embodiments of the invention, the average particle diameter of the plurality of particles of the at least one water-soluble anionic mucoadhesive polymer is from 40 to 400 microns. In certain other embodiments of the invention, the average particle diameter of the plurality of particles of the at least one water-soluble anionic mucoadhesive polymer is from 50 to 400 microns. In certain other embodiments of the invention, the average particle diameter of the plurality of particles of the at least one water-soluble anionic mucoadhesive polymer is from 50 to 300 microns.

In one embodiment of the invention, the ion-exchange composition comprises a buffering agent.

In one embodiment of the invention, the ion-exchange composition comprises a buffering agent selected from the group consisting of a tri(hydroxymethyl)aminomethane buffering agent, a phosphate buffering agent, a carbonate buffering agent and combinations thereof.

In one embodiment of the invention, the at least one water-soluble anionic mucoadhesive polymer is weakly acidic.

In one embodiment of the invention, the at least one water-soluble anionic mucoadhesive polymer comprises carboxylic functional groups.

In one embodiment of the invention, the at least one water-soluble anionic mucoadhesive polymer is selected from sulfonated polysaccharides and/or anionic polysaccharides and/or polyacrylic acid.

In one embodiment of the invention, the at least one water-soluble anionic mucoadhesive polymer is selected from the group consisting of xanthan gum, carrageenan, carbomer, carboxymethyl cellulose and combinations thereof. In one embodiment of the invention, the at least one water-soluble anionic mucoadhesive polymer is xanthan gum.

In one embodiment of the invention, the at least one water-soluble anionic mucoadhesive polymer includes a molecular weight (mw) of at least 80 kDa.

In certain other embodiments of the invention, the at least one water-soluble anionic mucoadhesive polymer includes a molecular weight (mw) of at least 50 kDa. In certain other embodiments of the invention, the at least one water-soluble anionic mucoadhesive polymer includes a molecular weight (mw) of at least 75 kDa. In certain other embodiments of the invention, the at least one water-soluble anionic mucoadhesive polymer includes a molecular weight (mw) of at least 100 kDa. In certain other embodiments of the invention, the at least one water-soluble anionic mucoadhesive polymer includes a molecular weight (mw) of at least 150 kDa. In certain other embodiments of the invention, the at least one water-soluble anionic mucoadhesive polymer includes a molecular weight (mw) of at least 200 kDa. In certain other embodiments of the invention, the at least one water-soluble anionic mucoadhesive polymer includes a molecular weight (mw) of at least 250 kDa.

In one embodiment of the invention, the at least one water-soluble anionic mucoadhesive polymer includes a molecular weight (mw) of 80 to 3500 kDa.

In one embodiment of the invention, the at least one water-soluble anionic mucoadhesive polymer includes a molecular weight (mw) of 80 to 600 kDa.

In certain other embodiments of the invention, the at least one water-soluble anionic mucoadhesive polymer includes a molecular weight (mw) of 50 to 700 kDa. In certain other embodiments of the invention, the at least one water-soluble anionic mucoadhesive polymer includes a molecular weight (mw) of 100 to 600 kDa. In certain other embodiments of the invention, the at least one water-soluble anionic mucoadhesive polymer includes a molecular weight (mw) of 150 to 700 kDa. In certain other embodiments of the invention, the at least one water-soluble anionic mucoadhesive polymer includes a molecular weight (mw) of 200 to 600 kDa. In certain other embodiments of the invention, the at least one water-soluble anionic mucoadhesive polymer includes a molecular weight (mw) of 250 to 500 kDa.

In one embodiment of the invention, the oral tablet disintegrates in at most 2 minutes in contact with saliva.

In one embodiment of the invention, the oral tablet disintegrates in at most 1 minute in contact with saliva.

In one embodiment of the invention, the oral tablet disintegrates in at most 30 seconds in contact with saliva.

In certain other embodiments of the invention, the oral tablet disintegrates in at most 90 seconds in contact with saliva. In certain other embodiments of the invention, the oral tablet disintegrates in at most 75 seconds in contact with saliva. In certain other embodiments of the invention, the oral tablet disintegrates in at most 45 seconds in contact with saliva. In certain other embodiments of the invention, the oral tablet disintegrates in at most 20 seconds in contact with saliva. In certain other embodiments of the invention, the oral tablet disintegrates in at most 10 seconds in contact with saliva.

In one embodiment of the invention, the oral tablet is an orally disintegrating tablet (ODT). In one embodiment of the invention, the oral tablet is a fast disintegrating tablet (ODT).

In one embodiment of the invention, the oral tablet is a chewable tablet. In this embodiment, the oral tablet is to be chewed upon oral administration.

In one embodiment of the invention, the oral tablet comprises the ion-exchange composition in an amount of 0.1 to 25% by weight of the tablet. In one embodiment of the invention, the oral tablet comprises the ion-exchange composition in an amount of 0.5 to 25% by weight of the tablet. In one embodiment of the invention, the oral tablet comprises the ion-exchange composition in an amount of 1 to 25% by weight of the tablet. In one embodiment of the invention, the oral tablet comprises the ion-exchange composition in an amount of 1 to 20% by weight of the tablet. In one embodiment of the invention, the oral tablet comprises the ion-exchange composition in an amount of 5 to 25% by weight of the tablet. In one embodiment of the invention, the oral tablet comprises the ion-exchange composition in an amount of 5 to 20% by weight of the tablet.

In one embodiment of the invention, the oral tablet comprises a buffering agent in an amount of 1 to 5% by weight of the tablet.

In one embodiment of the invention, the oral tablet comprises a buffering agent selected from the group consisting of a tri(hydroxymethyl)aminomethane buffering agent, a phosphate buffering agent, a carbonate buffering agent and combinations thereof.

In one embodiment of the invention, the oral tablet comprises nicotine in an amount of 0.5 to 8.0 mg.

In one embodiment of the invention, the oral tablet comprises nicotine in an amount of 1.0 to 4.0 mg. In one embodiment of the invention, the oral tablet comprises nicotine in an amount of 1.0 to 3.0 mg. In one embodiment of the invention, the oral tablet comprises nicotine in an amount of 2.0 to 4.0 mg.

In one embodiment of the invention, the oral tablet comprises the one or more sugar alcohol particles in an amount of at least 40% by weight of the tablet.

In one embodiment of the invention, the oral tablet comprises the one or more sugar alcohol particles in an amount of at least 60% by weight of the tablet.

In one embodiment of the invention, the one or more sugar alcohol particles comprises sugar alcohols selected from sorbitol, erythritol, xylitol, lactitol, maltitol, mannitol, isomalt, and combinations thereof.

In one embodiment of the invention, the one or more sugar alcohol particles comprises directly compressible (DC) and non-directly compressible (non-DC) sugar alcohol particles.

In one embodiment of the invention, the one or more sugar alcohol particles comprises non-DC sugar alcohol particles in an amount of at least 30% by weight of the tablet.

In one embodiment of the invention, the one or more sugar alcohol particles comprises non-DC sugar alcohol particles selected from non-DC particles of erythritol, maltitol, xylitol, isomalt, and combinations thereof.

In one embodiment of the invention, the one or more sugar alcohol particles comprises at least 20% by weight of non-DC sugar alcohol particles with a particle size above 500 μm.

In one embodiment of the invention, the one or more sugar alcohol particles comprises DC sugar alcohol particles in an amount of at least 30% by weight of the tablet.

In one embodiment of the invention, the one or more sugar alcohol particles comprises directly compressible (DC) and non-directly compressible (non-DC) sugar alcohol particles present in the tablet in a weight ratio between said non-DC sugar alcohol particles and said DC sugar alcohol particles of 0.2 and 1.2.

In one embodiment of the invention, the one or more sugar alcohol particles is tableted into a first module and combined with a second population of particles that is tableted into a second module, and wherein the second module is different in composition than the first module.

In one embodiment of the invention, the one or more sugar alcohol particles is tableted into a first module and combined with a second population of particles that is tableted into a second module, and wherein the first module includes said ion-exchange composition.

In one embodiment of the invention, the one or more sugar alcohol particles is tableted into a first module and combined with a second population of particles that is tableted into a second module, and wherein the second module includes gum base.

In one embodiment of the invention, the oral tablet further comprises a disintegrant.

In one embodiment of the invention, the oral tablet further comprises a disintegrant in an amount of 1 to 10% by weight of the tablet.

In one embodiment of the invention, the oral tablet further comprises a disintegrant of cross-linked polyvinylpyrrolidone.

In one embodiment of the invention, the ion-exchange composition forms a gel in contact with the oral mucosa when hydrated with saliva.

In certain other aspects of the invention, there is provided an ion-exchange composition for oromucosal delivery of biologically active compounds, the composition comprising a plurality of particles of at least one water-soluble anionic mucoadhesive polymer loaded with a cationic biologically active compound.

In one embodiment of this aspect, the ion-exchange composition is a powder.

In one embodiment of this aspect, the ion-exchange composition is included in a tablet.

In one embodiment of this aspect, the ion-exchange composition is included in a sachet.

In one embodiment of this aspect, the ion-exchange composition is made by providing a water slurry of the at least one water-soluble anionic mucoadhesive polymer, adding nicotine and optionally a buffering agent, and evaporating water from the slurry to obtain a final water content below 10% by weight of the composition.

In one embodiment of this aspect, the ion-exchange composition is made by providing a water dispersion of the at least one water-soluble anionic mucoadhesive polymer, adding nicotine and optionally a buffering agent, and precipitating the composition from the dispersion by means of a suitable agent to obtain a final water content below 10% by weight of the composition.

In one embodiment of this aspect, the ion-exchange composition is made by using deionized water. In certain embodiments, divalent cations may be present in water that is not deionized. This may result in cross-linking which is not preferred according to the invention. In certain other embodiments, monovalent cations may be present in water that is not deionized. This may result in undesired ion-exchange competition with the biologically active compound. Hence, if the ion-exchange complex is saturated with monovalent cations, such as sodium ions, already before nicotine is introduced during manufacture, it may have an adverse impact on properties such as loading properties of the ion-exchange resin, stability and release functionalities. It is contemplated that for instance if a sodium alginate salt is loaded with nicotine, such adverse impact may be present.

In one embodiment of this aspect, the ion-exchange composition is composed according to the embodiments of the tablet.

In certain other aspects of the invention, there is provided an ion-exchange composition for oromucosal delivery of nicotine, the composition comprising a plurality of particles of at least one polacrilex resin loaded with nicotine, the polacrilex resin being at least partly coated with at least one water-soluble anionic mucoadhesive polymer.

In one embodiment of this aspect, the at least one water-soluble anionic mucoadhesive polymer is composed according to the embodiments of the tablet.

In certain other aspects of the invention, there is provided a method of oromucosal delivery of biologically active compounds, the method comprising the steps of i) providing an oral formulation including an ion-exchange composition comprising a plurality of particles of at least one water-soluble anionic mucoadhesive polymer loaded with a cationic biologically active compound, ii) disintegrating the oral formulation in contact with saliva without substantially hydrating said polymer particles, iii) contacting at least a part of said polymer particles with the oral mucosa, iv) forming a gel in contact with the oral mucosa by hydrating said polymer particles with saliva, and v) delivering the biologically active compound to the oral mucosa from said polymer particles.

In one embodiment of this aspect, the ion-exchange composition is composed according to the embodiments of the tablet.

DETAILED DESCRIPTION

Figures 1, 2:
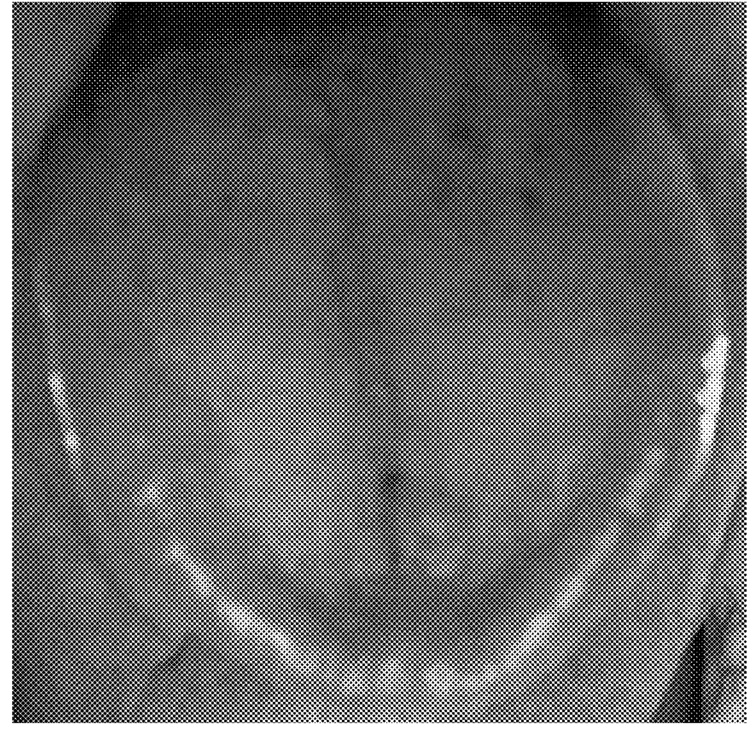
FIG. 1 is an illustration of the properties of the particles of the water-soluble anionic mucoadhesive polymer according to the invention. Two series of experiments were conducted where particles of a water-soluble anionic mucoadhesive polymer were added to a petri dish containing 1 ml of aqua purificata. In experiment G(IPA), a powder according to Example 3 was applied. In experiment G, a powder according to Example 1 was applied. Pictures were taken initially (T0), after 5 minutes (T−5 min), after 10 minutes (T−10 min) and with additional water added after 10 minutes. The powder was precipitated in the water and was seen as blue discrete areas on the bottom of the petri dish.
FIG. 2 is an illustration of adherence to the oral mucosa according to the invention. A tablet made in accordance with Example 14-4 was administered to a subject, where the ion-exchange composition was exchanged with the particles of Example 1 having a blue color. After 5 minutes, the coloring was monitored for the subject.

Accordingly, the present invention provides an oral tablet for oromucosal delivery of biologically active compounds, the tablet comprising a sugar alcohol composition comprising one or more sugar alcohol particles in an amount of at least 20% by weight of the tablet, an ion-exchange composition comprising a plurality of particles of at least one water-soluble anionic mucoadhesive polymer loaded with a cationic biologically active compound.

As used herein the term "oral tablet" is considered as a tablet for oral use. Particularly, the oral tablet is considered as formed by tableting, i.e. compression of a particle composition. Typically, the oral tablet may also be referred to as a tablet.

The term "weight of the oral tablet" or similar wording meaning the same is defined in the present context as weight of the oral tablet, not including the weight of an outer coating, such as a hard coating, soft coating, and the like.

As used herein, the term "%" and "percent" refers to percent by weight, unless otherwise is stated.

As used herein, the term molecular weight or Mw (mw) is intended to mean weight average molecular weight.

The term "sustained release" or "extended release" is herein intended to mean prolonged release over time. The term "rapid release" or "quick release" or "high release" is herein intended to mean a higher content released for a given period of time. The term "controlled release" is intended to mean a release of a substance from an oral tablet by the aid of active use of the oral tablet in the oral cavity of the subject, whereby the active use is controlling the amount of substance released.

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one". Additionally, the words "a" and "an" when used in the present document in connection with the word comprising or containing denote "one or more." The expression "one or more" is intended to mean one, two, three or more.

In the present context, the term "mucoadhesion" or simply "adhesion" is used to describe when two surfaces, one of which is mucus or a mucous membrane and the other typically the surface of a drug delivery system, are held together for extended periods of time by interfacial forces.

By "ion-exchange" is meant a complex (loose association) formed between a biologically active compound and the polymer according to the invention, is meant the complex formed between the functional groups of the biologically active compound (e.g. amine and pyridine) and the functional groups of the polymers according to the invention (e.g. sulfate, alcohol and carboxylate etc.), is meant the non-covalent bond formed between the biologically active compound and the polymer according to the invention (e.g. ionic interaction and hydrogen bonding). The complexation between the biologically active compound and the polymer according to the invention may be affected by the environment (e.g. pH, solvent, concentrations and temperature).

The term "non-DC sugar alcohol particles" refers to particles of non-directly compressible (non-DC) sugar alcohol. It is noted that the terms "non-DC sugar alcohol particles" and "non-DC particles" are used interchangeably. In the present context, the non-DC sugar alcohol particles refers to particles which have not been preprocessed by granulation with e.g. other sugar alcohols or binders for the purpose of obtaining so-called direct compressible particles (DC). In the present context, non-DC sugar alcohol particles include particles obtained by crystallization followed by milling which does not involve other sugar alcohols or binders. Thus, non-DC sugar alcohol particles are considered as particles consisting of non-DC sugar alcohol.

In the present context, the term "non-DC areas" refers to small volumes or spaces formed during tableting from the non-DC particles of non-DC sugar alcohol. Moreover, each of the non-DC areas may be composed of a single non-DC sugar alcohol particle or may comprise several non-DC sugar alcohol particles. When the non-DC areas are distinct, i.e. not diffuse, the non-DC areas may be evenly distributed in the tablet, or at least one module thereof when the tablet comprises two or more modules. In such embodiments, where the non-DC areas are evenly distributed in in the tablet, or at least one module thereof, the non-DC areas may thus facilitate an even saliva generation in the mouth upon mastication.

The term "DC sugar alcohol particles" refers to particles of direct compressible (DC) sugar alcohol. It is noted that the terms "DC sugar alcohol particles" and "DC particles" are used interchangeably. DC sugar alcohol particles may be obtained e.g. as particles of sugar alcohols having DC grade by nature, e.g. sorbitol, or by granulating non-DC sugar alcohol with e.g. other sugar alcohols or binders for the purpose of obtaining so-called direct compressible particles (DC). Also, granulation of non-DC sugar alcohol with water as binder is considered to result in "DC sugar alcohol particles" in the present context.

As used herein, the term "orally disintegrating tablet" or "ODT" is intended to mean a tablet as understood by a skilled person within the art of ODT tablets, i.e. a solid dosage form that disintegrates rapidly (within seconds) without water when placed on the tongue.

As used herein, the term “fast disintegrating tablet” or “FDT” is intended to mean a tablet as understood by a skilled person within the art of FDT tablets, i.e. a solid dosage form that disintegrates rapidly (within seconds) without water when placed on the tongue.

As used herein, the term “disintegrate” refers to a reduction of a said object to components, fragments or particles. Disintegration time is measured in vitro. The in vitro measurements are carried out in accordance to European Pharmacopeia 9.0, section 2.9.1, Disintegration of tablets and capsules.

As used herein, the term “dissolve” is the process where a solid substance enters a solvent (oral saliva) to yield a solution. Unless otherwise stated, dissolving implies a full dissolving of the compound in question.

As used herein, the terms “disintegrant” refers to an ingredient facilitating disintegration of an orally disintegrating tablet, when the orally disintegrating tablet comes into contact with saliva. Disintegrants usable within the scope of the invention may include starch, pregelatinized starch, modified starch (including potato starch, maize starch, starch 1500, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate. Disintegrants may often be considered as measure promoting the break-up of the dosage form into smaller fragments upon administration to allow the onset of drug dissolution and eventual absorption.

As used herein, the term “pH regulating agent” refers to agents that actively adjust and regulate the pH value of the solution to which they have been added or are to be added. Thus, pH regulating agents may be acids and bases, including acidic buffering agents and alkaline buffering agents. On the other hand, pH regulating agents does not including substances and compositions that can only affect the pH by dilution. Furthermore, pH regulating agents does not include e.g. flavoring, fillers, etc.

As used herein, the term “buffering agent” is used interchangeably with “buffer” and refers to agents for obtaining a buffer solution. Buffering agents include acidic buffering agents, i.e. for obtaining a buffer solution with an acidic pH, and alkaline buffering agents, i.e. for obtaining a buffer solution with an alkaline pH.

When referring to induced saliva generation, the saliva generation is tested using the following method, unless stated otherwise. Test subject abstain from eating and drinking at least 30 minutes before initiation of any test. Immediately before introducing of the tablet into the oral cavity, the test subject swallows. The test subject refrains from swallowing during the test. Immediately after introducing of the tablet into the oral cavity, the test subject starts masticating the tablet at a frequency of 1 chew per second for 20 seconds. Then, saliva and any remains of the tablet is kept in the mouth within chewing for 10 second. 30 seconds after starting the test, the test subject discards saliva including any tablet fragments into a plastic cup, which is weighted. Saliva discarded also at 90 seconds after onset of mastication, at 180 seconds after onset of mastication, at 300 seconds after onset of mastication, at 420 seconds after onset of mastication, and at 600 seconds after onset of mastication. At all times, the test subject makes as little movement as possible, and refrains from swallowing.

As used herein, the term “particle size” refers to the average particle size as determined according to European Pharmacopoeia 9.1 when using test method 2.9.38 particle size distribution estimation by analytical sieving, unless otherwise specifically is mentioned.

As used herein the term “biologically active ingredient” or simply “active ingredient” refers to a substance that is biologically active and has a physiological effect on the human body for the benefit of the human body or part thereof. Active ingredients include active pharmaceutical ingredients, but also other active substances such as nutraceuticals.

The term “release” in the present context is intended to mean tested under “in vivo” conditions, if not stated otherwise. In the present context, when the tablet is masticated, “in vivo” conditions is intended to mean that a sample is masticated with a chewing frequency of 60 chews pr. minute for a certain period of time in a test panel of 8 test persons, if not stated otherwise. These test persons abstain from eating and drinking at least 30 minutes before initiation of any test. The test persons are healthy persons appointed on an objective basis according to specified requirements.

By the terms “water-insoluble gum base” or “gum base” or “gum base matrix” or similar wording is meant the mainly water-insoluble ingredients and hydrophobic gum base ingredients. The “gum base” may contain gum base polymers and plasticizers, waxes, emulsifiers, fats and/or fillers.

As used herein, the term “nicotine” refers to nicotine in any form, including free base nicotine, nicotine salts, nicotine bound to ion exchange resins, nicotine bound to zeolites; nicotine bound to cellulose, such as microcrystalline cellulose, such as of microbial origin, or starch microspheres, nicotine bound to CaCO3, and mixtures thereof. Thus, when referring to nicotine amounts, the amounts refers to the amount of pure nicotine. Thus, when measuring the concentration of nicotine added as nicotine salt, it is the mass of the equivalent amount of pure nicotine, not the mass of the salt, that is relevant.

As used herein, the term “nicotine salt” refers to nicotine in ionized form bonded electrostatically to a counterion.

In an embodiment of the invention, the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and hydrates thereof (e.g., nicotine zinc chloride monohydrate).

In an embodiment of the invention, the nicotine salt comprises nicotine bitartrate. In the present context, nicotine bitartrate includes hydrates thereof. According to an embodiment of the invention, the nicotine salt is a water-soluble nicotine salt. In the present context, the term “water-soluble salt” is understood as a salt having a solubility in water of at least 10 g of salt per 100 mL water at standard lab conditions, including temperature of 25 degrees Celsius, atmospheric pressure, and pH of 7. Also, it should be understood that the when the nicotine comprises nicotine salt, possibly in combination with other forms of nicotine, the nicotine salt may consist of only one nicotine salt or may be a combination of two or more nicotine salts. In an embodiment of the invention, the nicotine is provided as free nicotine base.

As used herein, the term “release of nicotine” refers to the nicotine being made bioavailable, i.e. available for absorption over the mucous membrane in the oral cavity. While some forms of nicotine require dissolution for being bioavailable, other forms may be readily absorbed into the body without dissolution.

As used herein, the term "NBT" refers to nicotine bitartrate and hydrates thereof.

Nicotine (NCT) is the main alkaloid found in tobacco and responsible for an addictive potential. NCT can be found in both its free base form as a liquid, or as an ionic complex in the form of a salt with a counter ion e.g., chloride ion (Cl—) or sulphate ion (HSO4−).

By prolonged intraoral drug residence time for NCT it is meant that the nicotine is present in the oral cavity for a longer time than shown for formulations which do not comprise a mucoadhesive nicotine complex formulation according to the present invention. Further, prolonged intraoral drug residence time for NCT can also be meant as that the entire amount of nicotine is not washed off the oromucosa within the first 2 minutes, or within the first 5 minutes or within the first 10 minutes. By the present invention the NCT may be present in amount of more than 20%, such as 30%, such as 40%, such as 50%, such as 60%, such as 70%, such as 80%, such as 90% in the buccal cavity for more than 10 minutes. By the present invention the NCT may be present in amount of more than 20%, such as 30%, such as 40%, such as 50%, such as 60%, such as 70%, such as 80%, such as 85% in the buccal cavity for more than 20 minutes.

Contrary to expectations, experiments have shown that the permeability of nicotine across the buccal mucosa decreases relatively little when increasing the concentration of nicotine. For example, experiments have shown that an increase in the concentration of nicotine from 100 microgram/mL to 14,000 microgram/mL results in a decrease of about a factor of two. This is highly surprising and is utilized by aiming for concentrations of nicotine in the oral cavity, which are much higher than previously seen or desired. The present delivery vehicle thus benefits and aims for very high nicotine content in the oral cavity, thereby increasing the nicotine uptake. Furthermore, it has been realized that the effect of nicotine concentrations is thus at least comparable to the effect of pH regulation in the oral cavity. This is contrary to any expectations.

In an embodiment of the invention, the oral tablet comprises nicotine and a pH regulating agent, wherein the formulation is designed to release the content of nicotine within a period of 90 seconds in contact with oral saliva and the formulation is designed to release the content of pH regulating agent within a period of 60 seconds in contact with oral saliva and wherein the formulation comprises nicotine in an amount of at least 0.5 mg, such as nicotine in an amount of between 0.5 mg and 8 mg wherein said nicotine is provided as nicotine salt, and wherein the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and hydrates thereof (e.g., nicotine zinc chloride monohydrate).

The above has been accomplished to the surprise of the inventors, as typical conventional products and conventional wisdom seek to delay the disintegration and delay the dissolution of nicotine.

The water-soluble anionic polymer used in the present invention can be either synthetic or natural. The water-soluble anionic polymer can be classified as linear, branched chain, crosslinked or network polymers. Preferably, the polymer is not cross-linked. The at least one mucoadhesive water-soluble anionic polymer may be linear polymer(s). The at least one mucoadhesive water-soluble anionic polymer may be branched chained polymer(s). The at least one mucoadhesive water-soluble anionic polymer may be cross bound polyacrylic acid polymer(s). The at least one mucoadhesive water-soluble anionic polymer may be selected from sulfated polysaccharides and/or anionic polysaccharides. Polysaccharides are polymers of monosaccharides that can origin from plants, seaweed extracts (e.g. carrageenans), or microorganisms (e.g. xanthan gum). The polysaccharides can be anionic (charged) and/or sulfated.

In one embodiment, the formulation comprises a combination of the at least one mucoadhesive water-soluble anionic polymers.

In one embodiment, the formulation comprises a combination of at least one xanthan gum and at least one carrageenan. In one embodiment the formulation comprises a combination of at least one xanthan gum and at least one carbomer. In one embodiment the formulation comprises a combination of at least one carrageenan and at least one carbomer.

Carrageenan is a family of linear sulphated polysaccharides. They are used for their gelling, thickening and stabilizing properties. There are three main varieties of carrageen, which differ in their degree of sulphation. Kappa-carrageen has one sulphate group per disaccharide, Iota-carrageen two, and Lambda-carrageen three. Gelcarins are carrageenans and are linear polymers.

Gelcarin® GP 379 NF is an Iota carrageenan, which can be used for gelling, thickening, and stabilizing applications.

Xanthan gum is a polysaccharide used as an additive for thickening. It is composed of repeating pentasaccharide units, comprising glucose, mannose and glucuronic acid. xanthan gums are branched chained polymers.

XANTURAL® 180 is an 80-mesh (180 μm) xanthan gum product suitable for use as a pharmaceutical excipient. It prevents phase separation in suspensions and emulsions, and ensures products are free-flowing throughout their shelf-life. XANTURAL® 180 is typically used in oral suspensions and syrups.

Carbomer is a high molecular weight, crosslinked polyacrylic acid polymer, which is sold e.g. under the brand Carbopol®. Carbopols are carbomers.

The ion-exchange composition or oral formulation may further comprise at least one preservative. The at least one preservative may be selected from alcohols such as monoalcohols, diols or polyalcohols. In one embodiment the at least one preservative is an alcohol selected from ethanol or propylene glycol. The at least one preservative may be chlorhexidine.

In one embodiment, a buffer may be added to the ion-exchange composition or oral formulation to adjust the pH. Buffers may assist in facilitating nicotine absorption. The buffer can be selected from the group consisting of potassium carbonate, potassium bicarbonate, sodium carbonate and sodium bicarbonate, potassium citrate and dipotassium phosphate, or mixtures thereof.

In one embodiment of the invention, the formulation comprises nicotine that is not in complex with at least one mucoadhesive water-soluble anionic polymer.

In one embodiment of the invention, the at least one water-soluble anionic mucoadhesive polymer is carrageenan. In one embodiment of the invention, the at least one water-soluble anionic mucoadhesive polymer is a carbomer. In one embodiment of the invention, the at least one water-soluble anionic mucoadhesive polymer is carboxymethyl cellulose.

In one embodiment of the invention, the mucoadhesive oromucosal formulation according to the present invention may be administered to a human subject up to 80 times per day, such as up to 70 times per day, such as up to 60 times per day, such as up to 50 times per day or less. In one embodiment the mucoadhesive oromucosal formulation may be administered for up to 6 times every hour.

In an embodiment of the invention, the formulation further comprises a disintegrant.

In an embodiment of the invention, the disintegrant is selected from starch, pregelatinized starch, modified starch (including potato starch, maize starch, starch 1500, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate, and combinations thereof.

One advantage of the above embodiment may be that said disintegrant facilitates the disintegration and dissolution of the formulation, whereby a release of the nicotine and pH controlling agent is achieved.

In the present context, it should be understood that said use in the alleviation of nicotine craving involves administering said orally disintegrating nicotine tablet orally.

In one embodiment of the invention, the oral tablet comprises non-directly compressible (non-DC) sugar alcohol particles. The non-DC particles preferably provide the tablet with a plurality of discrete non-DC areas.

In the present context, the non-DC sugar alcohol particles are understood and defined by the skilled person with reference to their typical commercial trade grade. In an embodiment of the invention, the non-DC sugar alcohol particles have not been granulated prior to tableting. Thus, the non-DC sugar alcohol particles are provided as non-granulated particles.

These are typically available in a non-DC form of the relevant sugar alcohol as particles which have not been preprocessed by granulation with other sugar alcohols or binders for the purpose of obtaining so-called direct compressible particles (DC) on the basis of sugar alcohol particles which are by themselves not suitable for direct compression. Such non-DC particles of sugar alcohol may typically consist of the sugar alcohol. Therefore, non-DC sugar alcohol particles may typically be particles consisting of sugar alcohol, which is non-directly compressible in its pure form. Examples of sugar alcohols which are non-directly compressible when provided as particles consisting of the sugar alcohol in question include erythritol, xylitol, maltitol, mannitol, lactitol, isomalt, etc. Therefore, preferred non-DC grades of sugar alcohol may include pure sugar alcohol particles.

In an embodiment of the invention, the oral tablet comprises at least two modules, where the one or more sugar alcohol particles is tableted into a first module and combined with a second population of particles that is tableted into a second module, and wherein the second module is different in composition than the first module.

In an embodiment of the invention, the oral tablet comprises at least two modules, where the one or more sugar alcohol particles is tableted into a first module and combined with a second population of particles that is tableted into a second module, and wherein the first module includes said ion-exchange composition.

In the present context, "tableted into" is to be understood as also allowing other ingredients to be part of the tableted module. Hence, the module may comprise further ingredients apart from the one or more sugar alcohol particles.

In an embodiment of the invention, the oral tablet comprises at least two modules, where the one or more sugar alcohol particles comprises directly compressible (DC) and non-directly compressible (non-DC) sugar alcohol particles, which are is tableted into a first module and combined with a second population of particles that is tableted into a second module, and wherein the second module is different in composition than the first module.

In an embodiment of the invention, the oral tablet comprises at least two modules, where the one or more sugar alcohol particles comprises directly compressible (DC) and non-directly compressible (non-DC) sugar alcohol particles, which are is tableted into a first module and combined with a second population of particles that is tableted into a second module, and wherein the first module includes said ion-exchange composition.

One advantage of the above embodiment may be that the second module may have a higher mechanical strength, e.g. by means of a different composition comprising e.g. a very large amount of direct compressible ingredients, such as DC sugar alcohols.

A further advantage of the above embodiment may be that the second module may have a higher loading capacity for e.g. active ingredients, partly due to the higher obtainable mechanical strength achievable by large amounts of direct compressible ingredients, such as DC sugar alcohols.

Thus, in the above embodiment said population of particles is tableted into a first module, and wherein the tablet further comprises a second population of particles that is tableted into a second module. The first module may be tableted before the second module, or vice versa. In some embodiments, the tablet may comprise one or more further modules.

In an embodiment of the invention the oral tablet comprises at least two modules. A tablet comprising two or more modules will have module sizes which each are comparable to the volume of the complete tablet. Comparable in the present context means that the modules are not understood as small particles and a module should at least be greater than $1/20$ of the complete tablet volume, preferably greater than $1/10$ of the complete tablet volume.

In the present context, a module is intended to mean a plurality of particles being compressed together to form a gathered module of particles.

In an embodiment of the invention the oral tablet comprises a plurality of oral tablet modules. In the present context the application of e.g. two modules are in particular advantageous as the use of non-DC sugar alcohols by nature may result in a more fragile tablet or at least the module in which the non-DC sugar alcohols are. In other words, non-DC sugar alcohols may be present primarily in one module thereby optimizing the desired salivation and sensory experience from the module and the tablet as such whereas another module may serve as a support ensuring that the desired stability and friability of the complete tablet is obtained.

According to an embodiment of the invention, the tablet has two modules. Optionally, a coating may be applied around the two modules to form the final tablet.

An advantage of using two modules is described above, but it should also be noted that this effect may also be obtained when applying layers of very different nature. Such application may e.g. include the use of a gum module and a non-gum module, where the non-gum modules are containing the non-DC sugar alcohol particles. In this way, the non-gum layer may release the advantageous non-DC sugar alcohols and the gum layer may both stabilize the tablet as described above but also interact with the non-DC sugar alcohols during in particular the initial release for establishment of a very pleasant and impressing initial chew phase. This includes an increased saliva and moisture experience.

In an embodiment of the invention, the oral tablet comprises at least two modules, where the one or more sugar alcohol particles is tableted into a first module and combined with a second population of particles that is tableted into a second module, and wherein the second module includes gum base.

In an embodiment of the invention, the oral tablet comprises at least two modules, where the one or more sugar alcohol particles comprises directly compressible (DC) and non-directly compressible (non-DC) sugar alcohol particles, which are is tableted into a first module and combined with a second population of particles that is tableted into a second module, and wherein the second module includes gum base.

In an embodiment of the invention said population of particles is tableted into a first module and combined with a second population of particles that is tableted into a second module, and wherein the second module does not comprise non-DC sugar alcohol particles.

In one embodiment, the second population of particles comprises a large amount of DC sugar alcohols, such as larger amounts than the first population of particles. For example, the second population of particles may comprise at least 30% by weight of DC sugar alcohols, such as at least 50% by weight of DC sugar alcohols, such as at least 70% by weight of sugar alcohols. In an example embodiment, the second population of particles may comprise between 50 and 99.9% by weight of sugar alcohols, such as between 70 and 99% by weight of sugar alcohols. The amount of DC sugar alcohol may depend on the type and amount of active ingredient applied in the tablet.

In an embodiment of the invention said population of particles is tableted into a first module and combined with a second population of particles that is tableted into a second module, and wherein the second module is a an orally disintegrating tablet (ODT).

In an embodiment of the invention, the tablet is a chewable tablet.

In an embodiment of the invention, at least 20% by weight of the non-DC sugar alcohol particles have a particle size above 500 μm. In an embodiment of the invention, at least 30% by weight of the non-DC sugar alcohol particles have a particle size above 500 μm. In an embodiment of the invention, at least 40% by weight of the non-DC sugar alcohol particles have a particle size above 500 μm.

To the surprise of the inventor, it was seen that larger non-DC sugar alcohol particles were particularly beneficial according to the invention. In particular, larger non-DC sugar alcohol particles were seen to result in induced saliva generation, e.g. a higher total weight of saliva generated compared to smaller non-DC particles. Also, the perceived watering effect may be increased compared to smaller non-DC particles. These findings were not expected by the inventor.

In an embodiment of the invention, the non-DC sugar alcohol particles are non-DC erythritol particles. In an embodiment of the invention, the non-DC sugar alcohol particles are non-DC xylitol particles. In an embodiment of the invention, the non-DC sugar alcohol particles are non-DC isomalt particles.

In an embodiment of the invention, the tablet comprises said non-DC sugar alcohol particles in an amount of at least 10% by weight of the tablet. In an embodiment of the invention, the tablet comprises said non-DC sugar alcohol particles in an amount of at least 20% by weight of the tablet. In an embodiment of the invention, the tablet comprises said non-DC sugar alcohol particles in an amount of at least 30% by weight of the tablet. In an embodiment of the invention, the first module comprises said non-DC sugar alcohol particles in an amount of at least 30% by weight of the first module. In an embodiment of the invention, the first module comprises said non-DC sugar alcohol particles in an amount of at least 40% by weight of the first module.

In an embodiment of the invention, said DC sugar alcohol particles comprise sugar alcohols selected from DC particles of sorbitol, erythritol, xylitol, lactitol, maltitol, mannitol, isomalt, and combinations thereof. Sorbitol is an example of a sugar alcohol, which is considered DC grade, when provided as particles consisting of sorbitol, i.e. in its pure form.

On the other hand, several other sugar alcohols are considered non-DC grade if providing them as particles consisting of the specific sugar alcohol. Therefore, such non-DC sugar alcohols are conventionally processed into DC grade sugar alcohols, e.g. by granulating them with e.g. a binder. Examples of trade grades of DC sugar alcohols include sorbitol particles provided as e.g. Neosorb® 300 DC from Roquette, mannitol particles provided as e.g. Pearlitol® 300DC or Pearlitol 200 SD from Roquette, maltitol provided as e.g. SweetPearl® P 300 DC, xylitol provided as e.g. Xylisorb® 200 DC or Xylitab 200 from Dupont.

In an embodiment of the invention, the tablet comprises said DC sugar alcohol particles in an amount of at least 10% by weight of the tablet. In an embodiment of the invention, the tablet comprises said DC sugar alcohol particles in an amount of at least 20% by weight of the tablet. In an embodiment of the invention, the tablet comprises said DC sugar alcohol particles in an amount of at least 30% by weight of the tablet. According to an embodiment of the invention, said population of particles comprises DC sugar alcohol particles in an amount of at least 10% by weight. According to an embodiment of the invention, the first module comprises DC sugar alcohol particles in an amount of at least 10% by weight. According to an embodiment of the invention, the first module comprises said DC sugar alcohol particles in an amount of at least 10% by weight of the first module. According to an embodiment of the invention, the first module comprises said DC sugar alcohol particles in an amount of at least 30% by weight of the first module. In an embodiment of the invention, the second module comprises DC sugar alcohol particles in an amount of at least 30% by weight of the second module. In an embodiment of the invention, the second module comprises DC sugar alcohol particles in an amount of at least 50% by weight of the second module. In an embodiment of the invention, the second module comprises DC sugar alcohol particles in an amount of at least 70% by weight of the second module. In an embodiment of the invention, the second module comprises DC sugar alcohol particles in an amount of at least 90% by weight of the second module. In an embodiment of the invention the DC sugar alcohol particles in the second module are selected from DC particles of sorbitol, erythritol, xylitol, lactitol, maltitol, mannitol, isomalt, and combinations thereof.

In an embodiment of the invention, the tablet comprises one or more binders other than binders forming part of the DC sugar alcohol particles in an amount of 0.1 to 6% by weight of the tablet.

Suitable binders include Gum Arabic, Methyl Cellulose, Liquid glucose, Tragacanth, Ethyl Cellulose, Gelatin, Hydroxy Propyl Methyl Cellulose (HPMC), Starches, Hydroxy Propyl Cellulose (HPC), Pregelatinized Starch, Sodium Carboxy Methyl Cellulose (NaCMC), Alginic Acid, Polyvinyl Pyrrolidone (PVP), Maltodextrine (MD); Cellulose, Polyethylene Glycol (PEG), Polyvinyl Alcohols, Polymethacrylates, Copovidone or Microcrystalline Cellulose (MCC), alone or in combination.

According to an embodiment of the invention, the one or more binders comprises one or more cellulose binders. In an embodiment of the invention the one or more binders comprises microcrystalline cellulose (MCC), hydroxypropyl cellulose (HPC) or hydroxypropylmethyl cellulose (HPMC) or any combination thereof. In an embodiment of the invention the oral tablet comprises hydroxypropyl cellulose (HPC) binder in the amount of 0.1 to 6% by weight of the tablet, such as 0.1 to 5%, such as 0.1 to 4%, such as 0.1 to 3%, such as 0.1 to 2% by weight of the tablet. HPC may be applied as a particular attractive binder. Thus, this binder, when used with non-DC sugar alcohols such as erythritol, exhibits an advantageous sensory experience when compared to other well-known binders. In particular, the user of HPC lower than 4% by weight of the tablet is advantageous, such as 0.1 to 3%, such as 0.1 to 2% by weight of the tablet.

In an embodiment of the invention the non-DC sugar alcohol particles are particles that are not granulated, and the one or more binders are present as separate components in the tablet.

In an embodiment of the invention, the tablet has a weight ratio between said non-DC sugar alcohol particles and said DC sugar alcohol particles, which is between 0.2 and 1.2. In an embodiment of the invention, the tablet has a weight ratio between said non-DC sugar alcohol particles and said DC sugar alcohol particles, which is between 0.3 and 1.0. In an embodiment of the invention, the tablet has a weight ratio between said non-DC sugar alcohol particles and said DC sugar alcohol particles, which is between 0.3 and 0.7.

The weight ratio between non-DC sugar alcohol particles and DC sugar alcohol particles have proven significant according to an embodiment of the invention in the sense that a relatively high amount of non-DC sugar alcohol particles must be present in order to obtain the mouthfeel and taste obtained through the invention. However, this taste and mouthfeel also resides in the DC sugar alcohol particles. An example of such DC sugar alcohol particle is DC grade xylitol, which, together with the non-DC sugar alcohol particles may provide a mouthfeel which is unique and very attractive to test panels.

In an embodiment of the invention, the tablet comprises flavor. The amount of flavor may e.g. be from 0.1 to about 10% by weight of the tablet, such as 0.1 to about 6% by weight of the tablet.

Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), chili, cinnamon redhots, cotton candy, circus cotton candy, clove, coconut, coffee, clear coffee, double chocolate, energy cow, ginger, glutamate, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, MOUNTAIN DEW, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

In an embodiment of the invention, the tablet comprises particles comprising gum base, and wherein the tablet is designed to be masticated into a coherent residual containing water-insoluble components. In an embodiment of the invention, the oral tablet contains particles comprising gum base, and wherein the gum base comprises at least 5% by weight of elastomer.

The specific use of a relatively high proportion of elastomer in the gum base may effectively be used for modification of the release of active ingredients in terms of time and amount and the elastomer may also provide robust structure of the tablet facilitating that it is chewed into a coherent residual containing water-insoluble components. Some active ingredient may risk invoking disintegration of the residual whereas an elastomer may increase the coherence and compensate for the aggressive active ingredients. In an embodiment of the invention the gum base comprises at least 10% by weight of elastomer. In an embodiment of the invention the gum base comprises at least 15% by weight of elastomer. In an embodiment of the invention the gum base comprises between 15% and 25% by weight of elastomer. In an embodiment of the invention the gum base comprises between 17% and 23% by weight of elastomer. In an embodiment of the invention, the tablet is free of gum base.

In the following, raw materials will refer to the mixed particles to be compressed into a tablet according to embodiments of the invention unless otherwise stated.

The following description outlines explanations of how the tablet of the invention may be produced and further details of what may be added to the inventive composition.

Typically, the process of manufacture of the inventive tablet may be performed in a single tablet press, such as a rotary tablet press. But it may be a benefit under some circumstances to apply a separate tablet press. Preferably, the upper punch is convex which gives the upper face of the pressed tablet a concave form. It should of course be noted that the shape of the punches may vary depending of the desired tablet shape. In some embodiments of the invention, pressing of the tablets are performed at a force of 20 to 50 kN.

In a further embodiment, sucrose fatty acid esters may also be utilized for increased release of sweeteners including for instance the so-called highly potent sweeteners, such as for instance saccharin, cyclamate, aspartame, thaumatin, dihydrocalcones, stevioside, glycyrrhizin or salts or compounds thereof.

When including gum base in the formulation sugar alcohols typically constitute from about 5 to about 95% by weight of the tablet, more typically about 20 to about 80% by weight such as 30 to 70% or 30 to 60% by weight of the tablet.

In such an embodiment of the invention, the tablet further comprises, beside the already described sugar alcohols, materials selected from the group consisting of bulk sweeteners, flavors, dry-binders, tableting aids, anti-caking agents, emulsifiers, antioxidants, enhancers, absorption enhancers, buffers, high intensity sweeteners, softeners, colors, or any combination thereof.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the tablet formulation.

A tablet according to the invention may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono, di- and tri-calcium phosphates, cellulose polymers and combinations thereof.

EXAMPLES

The following non-limiting examples illustrate different variations of the present invention.

Example 1

Preparation of Ion-Exchange Composition Particles with Brilliant Blue

Aqua purificata (10 ml) was placed in a plastic beaker with a screw cap. A water-soluble anionic mucoadhesive polymer was slowly added to the water and the plastic beaker was closed with the cap before the dispersion was stirred at approximately 100° C. for 6 h. 1.5 ml of a 1% brilliant blue stock solution were added and the gel mixture was vigorously stirred for 1 h between 60° C. and 80° C. Precipitation was performed by pipetting 2 ml of the polymer gel with a positive displacement pipette into 30 ml of isopropyl alcohol (IPA) under stirring conditions. The supernatant was discarded. The precipitate was washed with fresh IPA until no coloring of the solvent could be observed. Residual water and IPA were evaporated from the precipitate until the structure of the product was substantially solid. The product was comminuted into given average particles dimensions.

Example 2

Preparation of Ion-Exchange Composition Particles with Brilliant Blue

Aqua purificata (10 ml) was placed in a plastic beaker with a screw cap. A water-soluble anionic mucoadhesive polymer was slowly added to the water and the plastic beaker was closed with the cap before the dispersion was stirred at approximately 100° C. for 6 h. 1.5 ml of a 1% brilliant blue stock solution were added and the gel mixture was vigorously stirred for 1 h between 60° C. and 80° C. Precipitation was performed by pipetting 2 ml of the polymer gel with a positive displacement pipette into 30 ml acetone under stirring conditions. The supernatant was discarded. The precipitate was washed with fresh acetone until no coloring of the solvent could be observed. Residual water and acetone were evaporated from the precipitate until the structure of the product was substantially solid. The product was comminuted into given average particles dimensions.

Example 3

Preparation of Ion-Exchange Composition Particles with Brilliant Blue

Isopropyl alcohol (30 ml) was placed in a plastic beaker with a screw cap. 3 ml of aqueous solution of brilliant blue (1%) were added. A water-soluble anionic mucoadhesive polymer was slowly added to the mixture and the plastic beaker was closed with the cap before the dispersion was stirred for 1 h. After 1 h standing time for sedimentation of the powder, the supernatant was poured off and discarded. IPA was evaporated from the residue resulting in a fine colored polymer powder.

Example 4A

Preparation of Ion-Exchange Composition Particles with Nicotine

Aqua purificata (10 ml) was placed in a plastic beaker with a screw cap. A water-soluble anionic mucoadhesive polymer was slowly added to the water and the plastic beaker was closed with the cap before the dispersion was stirred at approximately 100° C. for 6 h. L-Nicotine 99% was added, and the gel mixture was vortexed. Afterwards it was vigorously stirred for 1 h between 60° C. and 80° C. Precipitation was performed by pipetting 2 ml of the polymer gel with a positive displacement pipette into 30 ml isopropyl alcohol (IPA) under stirring conditions. The supernatant was poured off and discarded. Residual water and IPA were evaporated from the precipitate until the structure of the product was substantially solid. The product was comminuted into given average particles dimensions.

Example 4B

Preparation of Ion-Exchange Composition Particles with Nicotine

Isopropyl alcohol (30 ml) was placed in a plastic beaker with a screw cap. followed by the addition of nicotine. A water-soluble anionic mucoadhesive polymer was slowly added to the mixture and the plastic beaker was closed with the cap before the dispersion was stirred for 1 h. After 1 h standing time for sedimentation of the powder, the supernatant was poured off and discarded. IPA was evaporated from the residue resulting in a fine nicotine containing polymer powder.

Example 4C

Preparation of Ion-Exchange Composition Particles with Nicotine

Aqua purificata (10 ml) was placed in a plastic beaker with a screw cap. A water-soluble anionic mucoadhesive polymer was slowly added to the water and the plastic beaker was closed with the cap before the wetted powder was stirred at approximately 40° C. for 30 min. L-Nicotine 99% was added, where after the suspension was vigorously stirred for 1 h between 30° C. and 40° C. Water were evaporated from the suspension until the structure of the product was substantially solid. The product was comminuted into given average particles dimensions.

Example 5A

Preparation of Coated Brilliant Blue Polacrilex Resins with Water-Soluble Anionic Mucoadhesive Polymers Aqua purificata (10 mL) was placed in a plastic beaker with a screw cap. A water-soluble anionic mucoadhesive polymer was slowly added to the water and the plastic beaker was closed with the cap before the dispersion was stirred at approximately 100° C. for 6 h. In another plastic beaker aqua purificata (10 ml) was placed and brilliant blue stock solution (1%) was added. After addition of polacrilex resin (99%<300 microns) to the coloring solution (Amberlite IRP64 from Rohm and Haas, Paris, Cedex, France), the mixture was stirred at 100° C. for 6 h as well. Both solutions were mixed and immediately precipitated. Precipitation was performed by pipetting 2 ml of the polymer gel mixture with a positive displacement pipette into 30 ml isopropyl alcohol (IPA) under stirring conditions. The supernatant was discarded. The precipitate was washed with fresh IPA until no coloring of the solvent could be observed. Residual water and IPA were evaporated from the precipitate until the structure of the product was substantially solid. The product was comminuted into given average particles dimensions.

Example 5B

Preparation of Coated Nicotine Polacrilex Resins with Water-Soluble Anionic Mucoadhesive Polymers Aqua purificata (10 mL) was placed in a plastic beaker with a screw cap. A water-soluble anionic mucoadhesive polymer was slowly added to the water and the plastic beaker was closed with the cap before the dispersion was stirred at approximately 100° C. for 6 h and cooled. After addition of nicotine polacrilex resin (99%<300 microns and with a nicotine load of 15% by weight) to the solution (Amberlite IRP64 from Rohm and Haas, Paris, Cedex, France), the solution was precipitated. Precipitation was performed by pipetting 2 ml of the polymer gel mixture with a positive displacement pipette into 30 ml isopropyl alcohol (IPA) under stirring conditions. The supernatant was discarded. The precipitate was washed with fresh IPA. Residual water and IPA were evaporated from the precipitate until the structure of the product was substantially solid. The product was comminuted into given average particles dimensions. The resulting product had a nicotine content that was comparable to the content of the starting nicotine polacrilex resin.

Example 6

Preparation of Ion-Exchange Composition Particles with Different Types of Water-Soluble Anionic Mucoadhesive Polymers Different types of water-soluble anionic mucoadhesive polymers were applied in the methods of Examples 1-5 to obtain different ion-exchange composition particles.

TABLE 1

Different types of water-soluble anionic mucoadhesive polymers applied in Examples 1-5. Trade names given on specific polymers applied.

| Example | Polymer type | Trade name, Supplier | Particle size [mesh] |
|---|---|---|---|
| Ex6a | $_{r}$Carrageenan | Gelcarin GP 379 NF, FMC | 100 (min. 95%) |
| Ex6b | Xanthan gum | Xantural 180, CP Kelco | 80 |
| Ex6c | Carbomer | Carbopol 974P NF, Lubrizol | |
| Ex6d | Carbomer | Carbopol 71 G, Lubrizol | 40 (min. 95%) 100 (max. 10%) |
| Ex6e | Carbomer | Noveon AA-1 Polycarbophil, Lubrizol | |
| Ex6f | Carboxymethyl cellulose | Ac-Di-Sol, FMC | |
| Ex6g | Carboxymethyl cellulose | —, Sigma-Aldrich | |
| Ex6h | Polyacrylic acid | —, Aldrich | |

Example 7

Preparation of Ion-Exchange Composition Particles with Combined Polymers

To investigate the effect of the combination of different anionic mucoadhesive polymers, ion exchange composition particles with combined Carrageenan from Example 6a and xanthan gum from Example 6b were prepared in accordance with the methods of Examples 1-5.

TABLE 2

Different combinations of water-soluble mucoadhesive polymers applied in Examples 1-5.

| Example | Polymer type 1 | Polymer type 2 | Weight ratio |
|---|---|---|---|
| Ex7a | $_{r}$Carrageenan | Xanthan gum | 1:1 |
| Ex7b | $_{r}$Carrageenan | Xanthan gum | 2:1 |

Example 8

Preparation of Ion-Exchange Composition Particles with Different pH

To evaluate the impact of pH of polymer solution on precipitation, ion-exchange compositions with polyacrylic acid (450 kDa) from Example 6i were adjusted to different pH values by adding solutions of hydrochloric acid (1 M) or sodium hydroxide (1 M). Particles were prepared according to the methods of Examples 1-2.

TABLE 3

Different pH of polymer solutions adjusted with hydrochloric acid (1M) or sodium hydroxide (1M).

| Example | pH of polymer solution |
|---|---|
| Ex8a | 4 |
| Ex8b | 5 |
| Ex8c | 6 |
| Ex8d | 7 |
| Ex8e | 8 |
| Ex8f | 8.5 |

Example 9

Preparation of Ion-Exchange Composition Particles with Different Particle Sizes

In order to evaluate the effect of different particle size dimensions, ion-exchange compositions with Carrageenan from Example 6a were prepared in different average particle size diameters in accordance with the methods of Examples 1-5.

TABLE 4

Different average particle size diameters in accordance with the method of Examples 1-5.

| Example | Average particle size diameter |
|---|---|
| Ex9a | 10 microns |
| Ex9b | 20 microns |
| Ex9c | 50 microns |
| Ex9d | 100 microns |
| Ex9e | 200 microns |
| Ex9f | 500 microns |

Example 10

Preparation of Ion-Exchange Composition Particles with Different Nicotine Load

In order to evaluate the effect of the load of the cationic biologically active compound to the water-soluble anionic mucoadhesive polymers, nicotine was loaded in different charge ratios to carrageenan from Example 6a in accordance with the methods of Examples 1-5.

TABLE 5

Load of carrageenan to nicotine.

| Example | Charge ratio of carrageenan to nicotine |
|---|---|
| Ex10a | 0.5:1 |
| Ex10b | 1:1 |
| Ex10c | 2:1 |
| Ex10d | 4:1 |
| Ex10e | 6:1 |
| Ex10f | 10:1 |
| Ex10g | 20:1 |
| Ex10h | 30:1 |

Example 11

Preparation of Ion-Exchange Composition Particles with Different Molecular Weights In order to evaluate the effect of the molecular weight of the water-soluble anionic mucoadhesive polymers, different numbers of repeating units of polyacrylic acid from Example 6h were applied in accordance with the methods of Example 1-2.

TABLE 6

Different molecular weights of polyacrylic acid.

| Example | Molecular weight of polyacrylic acid |
|---|---|
| Ex11a | 450 kDa |
| Ex11b | 1250 kDa |
| Ex11c | 3000 kDa |

Example 12

Preparation of Oral Tablets with Different Compositions

Fast disintegrating tablet (FDT) formulations with ion-exchange composition particles (IE) were prepared based on Examples 1-11. The oral formulations were prepared with variations according to Examples 6-11.

Specific fast disintegrating tablet (FDT) formulations are exemplified below. The formulations were prepared with ion-exchange composition particles (IE) prepared in accordance with Example 4A. The water-soluble anionic mucoadhesive polymer was ι-Carrageenan (Ex6a) with an average particle size of 100 microns (Ex9d). The nicotine load was 1:4 (Ex10d). Punch used: 7.00 mm, circular, shallow concave, D tooling. Tablet weight: 100.0 mg.

TABLE 7

Fast disintegrating tablet compositions. Amounts are given in mg.

| | FDT(a) | FDT(b) | FDT(c) | FDT(d) | FDT(e) | FDT(f) |
|---|---|---|---|---|---|---|
| IE | 5.00 | 5.00 | 5.00 | 5.00 | 5.00 | 5.00 |
| Micro-crystalline cellulose | — | — | — | 39.1 | 39.1 | 39.1 |
| Mannitol DC | 79.2 | 79.2 | 79.2 | 39.1 | 39.1 | 39.1 |
| Crospovidone | 5.0 | — | — | 5.0 | — | — |
| Croscarmellose Sodium | — | 5.0 | — | — | 5.0 | — |
| Sodium Starch Glycolate | — | — | 5.0 | — | — | 5.0 |
| Peppermint | 4.0 | 4.0 | 4.0 | 4.0 | 4.0 | 4.0 |
| Menthol | 0.4 | 0.4 | 0.4 | 0.4 | 0.4 | 0.4 |
| Sucralose | 0.4 | 0.4 | 0.4 | 0.4 | 0.4 | 0.4 |
| Sodium carbonate | 5.0 | 5.0 | 5.0 | 5.0 | 5.0 | 5.0 |
| Silicium dioxide | — | — | — | 1.0 | 1.0 | 1.0 |
| Magnesium stearate | 1.0 | 1.0 | 1.0 | 1.0 | 1.0 | 1.0 |
| Total | 100.0 | 100.0 | 100.0 | 100.0 | 100.0 | 100.0 |

FDT = Fast disintegrating tablet.
IE = Ion-exchange composition particles.
DC = directly compressible.

The fast disintegrating tablets were manufactured on a lab scale machine, for example RIVA Piccola bi-layer tablet press. The tablet machine was commissioned by adjusting the fill depth and compression force so the weight and hardness of tablets match the acceptance criteria. A pre-compression force could be included to avoid capping.

TABLE 8

| Suggested start up parameters. | |
|---|---|
| Parameter | Target value |
| Speed | 10-20 rpm |
| Weight of FDT | 100 mg +/− 5% |
| Compression force | 2-8 kN |
| Thickness | N/A* |
| Friability (100 rpm) | <1% |

*The design of punches is not fixed. As the curvature impacts thickness, the thickness is not a fixed target at this time of development.

The acceptance criteria for friability should be fulfilled so packaging of the resulting fast disintegrating tablets is possible, but in this embodiment, the bulk sweetener and or filler should have relatively good compressibility and still have fast disintegration.

The fast disintegrating tablets according to the invention may comprise coloring agents. According to an embodiment of the invention, the fast disintegrating tablets may comprise color agents and whiteners such as FD&C-type dyes and lakes, fruit and vegetable extracts, titanium dioxide and combinations thereof.

Example 13

Preparation of Oral Tablets with Ready-to-Use Systems

Fast disintegrating tablet (FDT) formulations with ion-exchange composition particles (IE) were prepared based on Examples 1-11. The oral formulations were prepared with variations according to Examples 6-11.

Specific fast disintegrating tablet (FDT) formulations are exemplified below. The formulations were prepared with ion-exchange composition particles (IE) prepared in accordance with Example 4A. The water-soluble anionic mucoadhesive polymer were ι-Carrageenan (Ex6a) with an average particle size of 100 microns (Ex9d). The nicotine load was 1:4 (Ex10d). Punch used: 7.00 mm, circular, shallow concave, D tooling. Tablet weight: 100.0 mg.

Suitable for the purpose could be but not limited to: Pearlitol Flash (Roquette), Pharmaburst 500 (SPI Pharma), Ludiflash (BASF), ProSolv (JRS Pharma), ProSolv EasyTab (JRS Pharma), F-Melt (Fuji Chemical), SmartEx50 or SmartEx100 (Shin Etsu/Harke Pharma). These ready to use systems co-processed systems where filler, disintegrant, glidant or similar are implemented in the one powder mix. This saves handling of several excipients and ensures homogeneity between excipients.

TABLE 9

Fast disintegrating tablet compositions.

| | FDT(g) | FDT(h) | FDT(i) | FDT(j) | FDT(k) |
|---|---|---|---|---|---|
| IE | 5.00 | 5.00 | 5.00 | 5.00 | 5.00 |
| Ludiflash | 76.7 | — | — | — | — |
| Pearlitol Flash | — | 76.7 | — | — | — |
| SmartEx QD50 | — | — | 76.7 | — | — |
| F-Melt | — | — | — | 78.7 | — |
| ProSolv ODT G2 | — | — | — | — | 78.7 |
| Peppermint | 4.4 | 4.4 | 4.4 | 4.4 | 4.4 |
| Menthol | 1.5 | 1.5 | 1.5 | 1.5 | 1.5 |
| Sucralose | 0.4 | 0.4 | 0.4 | 0.4 | 0.4 |
| Sodium carbonate | 5.0 | 5.0 | 5.0 | 5.0 | 5.0 |
| Crospovidone | 5.0 | 5.0 | 5.0 | — | — |
| Croscarmellose Sodium | — | — | — | 3.0 | — |
| Sodium Starch Glycolate | — | — | — | — | 3.0 |
| Magnesium stearate | 2.0 | 2.0 | 2.0 | 2.0 | 2.0 |
| Total | 100.0 | 100.0 | 100.0 | 100.0 | 100.0 |

Amounts are given in mg.

FDT = Fast disintegrating tablet.

IE = Ion-exchange composition particles.

Example 14

Preparation of Oral Chewable Tablets

Chewable tablet formulations with ion-exchange composition particles (IE) were prepared based on Examples 1-11. The oral formulations were prepared with variations according to Examples 6-11.

Specific chewable tablet formulations are exemplified below. The formulations were prepared with ion-exchange composition particles (IE) prepared in accordance with Example 4A. The water-soluble anionic mucoadhesive polymer were i-Carrageenan (Ex6a) with an average particle size of 100 microns (Ex9d). The nicotine load was 1:4 (Ex10d). Punch used: 7.00 mm, circular, shallow concave, D tooling. Tablet weight: 100.0 mg.

TABLE 10

Oral tablet compositions for first layer of bi-layer tablets containing variants of non-DC sugar alcohols.

| Raw material (wt %) First layer | Ex14-1 | Ex14-2 | Ex14-3 | Ex14-4 | Ex15-5 | Ex14-6 |
|---|---|---|---|---|---|---|
| IE | 1.11 | 1.11 | 1.11 | 1.11 | 1.11 | 1.11 |
| Non-DC Xylitol | 50 | — | — | — | — | — |
| Sorbitol** | — | 50 | — | — | — | — |
| Non-DC Isomalt | — | — | 50 | — | — | — |
| Non-DC Erythritol | — | — | — | 50 | — | — |
| Non-DC Mannitol | — | — | — | — | 50 | — |
| Non-DC Maltitol | — | — | — | — | — | 50 |
| DC Isomalt | 42.64 | 42.64 | 42.64 | 42.64 | 42.64 | 42.64 |
| Flavor | 4 | 4 | 4 | 4 | 4 | 4 |
| HIS | 0.25 | 0.25 | 0.25 | 0.25 | 0.25 | 0.25 |
| Magnesium Stearate | 1 | 1 | 1 | 1 | 1 | 1 |
| Binder HPC | 1 | 1 | 1 | 1 | 1 | 1 |
| Resistance to crunch [N]* | 160 | >350 | 190 | 142 | 90 | 174 |
| Friability | 0.74 | 0.25 | 0.63 | 1.30 | 1.45 | 1.00 |

Amounts are given in wt-% of the respective layer of the tablet.

*Method limitation means maximum resistance to crunch which can be measured up to 350N.

**non-granulated sorbitol.

IE = Ion-exchange composition particles.

TABLE 11

Oral tablet compositions for first layer of bi-layer tablets containing variants of non-DC sugar alcohols.

| Raw material (wt %) First layer | Ex14-7 | Ex14-8 | Ex14-9 | Ex14-10 | Ex14-11 | Ex14-12 |
|---|---|---|---|---|---|---|
| IE | 0.56 | 0.56 | 0.56 | 0.56 | 0.56 | 0.56 |
| Non-DC Xylitol | 50 | — | — | — | — | — |
| Sorbitol** | — | 50 | — | — | — | — |
| Non-DC Isomalt | — | — | 50 | — | — | — |
| Non-DC Erythritol | — | — | — | 50 | — | — |
| Non-DC Mannitol | — | — | — | — | 50 | — |
| Non-DC Maltitol | — | — | — | — | — | 50 |
| Sorbitol | 43.69 | 43.69 | 43.69 | 43.69 | 43.69 | 43.69 |
| Flavor | 4 | 4 | 4 | 4 | 4 | 4 |
| HIS | 0.25 | 0.25 | 0.25 | 0.25 | 0.25 | 0.25 |
| Magnesium Stearate | 1 | 1 | 1 | 1 | 1 | 1 |
| Binder HPC | 0.5 | 0.5 | 0.5 | 0.5 | 0.5 | 0.5 |
| Resistance to crunch [N]* | 190 | >350 | 270 | 170 | 120 | 210 |
| Friability | 0.65 | 0.12 | 0.87 | 1.13 | 1.25 | 0.88 |

Amounts are given in wt-% of the respective layer of the tablet.

*Method limitation means maximum resistance to crunch which can be measured up to 350N.

**non-granulated sorbitol.

IE = Ion-exchange composition particles.

TABLE 12

Oral tablet compositions for the second layer of bi-layered tablets.

| Rw material (wt %) Second layer | Ex14-1-14-12 | Ex14-13-14-24 | Ex14-25-14-36 |
|---|---|---|---|
| DC Maltitol | 94.75 | — | — |
| DC Xylitol | — | 94.75 | — |
| DC Isomalt | — | — | 94.75 |
| Flavor | 4 | 4 | 4 |
| HIS | 0.25 | 0.25 | 0.25 |
| Magnesium Stearate | 1 | 1 | 1 |

Amounts are given in wt-% of the respective layer of the tablet.

TABLE 13

Oral tablet compositions for bi-layered tablets containing variants of DC-sugar alcohols.

| | Ex14-37 | Ex14-38 |
|---|---|---|
| Raw material (wt %) First layer | | |
| Non-DC Erythritol | 50 | 50 |
| DC Isomalt | 43.75 | 43.75 |
| Flavor | 4 | 4 |
| HIS | 0.25 | 0.25 |
| Magnesium Stearate | 1 | 1 |
| Binder HPC | 1 | 1 |
| Raw material (wt %) Second layer | | |
| IE | 0.56 | 0.56 |
| DC Erythritol | 94.19 | — |
| DC Mannitol | — | 94.19 |
| Flavor | 4 | 4 |
| HIS | 0.25 | 0.25 |
| Magnesium Stearate | 1 | 1 |
| Resistance to crunch [N]* | 140 | 182 |
| Friability | 1.25 | 1.68 |

Amounts are given in wt-% of the respective layer of the tablet.

*Method limitation means maximum resistance to crunch which can be measured up to 350N.

IE = Ion-exchange composition particles.

Process Flow

The compositions indicated in the above Tables 10 and 11 and 12 are each processed into two-layer tablets with compositions as outlined in Ex14-1-14-12, 14-13-14-24 and 14-25-14-36. In other words, the Ex14-1-14-12 are bi-layer tablet with a first layer according to Table 10 and 11 and the second layer is based primarily on DC maltitol. In Ex14-13-14-24, the second layer is primarily based on DC Xylitol. In Ex14-25-14-36, the second layer is primarily based on DC isomalt as shown in Table 12.

The composition of Table 13 is likewise processed into corresponding two-layer tablets of each of the compositions as indicated Ex14-37 and Ex14-38.

For each Ex14-1-14-38 the raw materials are sieved with a 1600-micron sieve and then weighed into the proper amount according to the exampled compositions of Tables 10 to 13.

The weighed amounts are then added to a Turbula mixer in a stainless-steel container and blended at 50 rpm for 5 minutes. MgSt was added after 4 minutes of blending.

The mixtures are then tableted by means of a Piccola RIVA DC-SC-041-2 or a Fette 3090i.

The applied molds have circular cross sections with diameters of 16 mm and are hollowed to produce tablets, which are concave and/or curved. Evidently, other mold size and shapes may be applied within the scope of the invention.

The resulting tablets according to Ex14-1-14-38 are then obtained by tableting with a suitable pressure force.

For each tablet of Ex14-1-14-38, the second layer as outlined in Table 12 and referred to as the second layer in Table 13 is pressed initially at a first relatively low pressure. The blended composition of the so-called first layer, i.e. compositions of Tables 10 and 11 and the first layer of Table 13 is then fed to the mold and a final two-layer tablet is then compressed at higher pressure than the pressure applied on the first layers, thereby producing final two-layer tablets according to Ex14-1-14-38. It is noted that the final two-layer tablets of Ex14-1-14-38 are 1.8 grams tablets and that the first layer of the tablets weighs 0.9 and the second layer of the tablets weighs 0.9 gram.

A specification of relevant compounds applied in the examples explained above are listed below.

HPC: Hydroxy propyl cellulose. Klucel Nutra D from Ashland

Non-DC Xylitol: Xivia C from Dupont

Non-granulated Sorbitol from PharmSorbidex from Cargill

Non-DC Isomalt: Isomalt GS from Beneo Paltinit

Non-DC Mannitol: Pearlitol from Roquette

Non-DC Maltitol: Maltisorb. P200 from Roquette

Non-DC Erythritol: Zerose 16952 from Cargill

DC Erythritol—Zerose 16966 from Cargill

DC Xylitol—Xylitab 200 from Dupont

DC Isomalt—Isomalt DC 101 from Beneo Paltinit

DC Mannitol—Pearlitol SD200 from Roquette

DC Maltitol—Sweetpearl 300 DC from Roquette

Ex14-39-14-41

TABLE 14

Compositions for 1.8 gram oral tablets.

| Raw material (wt %) I layer | Ex14-39 | Ex14-40 | Ex14-41 |
|---|---|---|---|
| IE | 0.56 | 0.56 | 0.56 |
| DC Isomalt | 44.44 | 34.44 | — |
| Non-DC Erythritol | 48.75 | 43.75 | 48.75 |
| DC CaCO3 | — | 15 | 44.44 |
| Flavor | 4 | 4 | 4 |
| HIS | 0.25 | 0.25 | 0.25 |
| Magnesium Stearate | 1 | 1 | 1 |
| Binder HPC | 1 | 1 | 1 |

Amounts are given in wt-% of the tablet.
IE = Ion-exchange composition particles.

All ingredients were received in powder form.

DC Isomalt—Isomalt DC 101 from Beneo Paltinit

Non-DC Erythritol: Zerose 16952 from Cargill

HPC: Hydroxy propyl cellulose. Klucel Nutra D from Ashland

DC CaCO3: Scoralite 97 PVP from Scora

Process Flow

For each of the Ex14-39-14-41 the raw materials are sieved with a 1600-micron sieve and then weighed into the proper amount according to the exampled compositions of Table 14.

For each example the weighed amounts are then added to a Turbula mixer in a stainless-steel container and blended at 50 rpm for 4 minutes and then adding magnesium stearate and blending one additional minute.

The resulting tablets according to Ex14-39-14-41 are then obtained by tableting the mixtures by means of a Piccola RIVA DC-SC-041-2. A Fette 3090i may also applied.

Evaluation

TABLE 15

Sensory evaluation of Ex14-13-14-18.

| Ex | Total sensory experience Good/ Acceptable(Acc)/Poor | Suitable Fast dissolving Chewable tablet | Initial Watering effect 1-5 1 low 5 high |
|---|---|---|---|
| 14-13 | Acc | A bit hard initial chew, disintegrate with crunchy feeling, many big particles for a long time | 4 |
| 14-14 | Poor | Unacceptable hard chew - not chewable or complete dissolvable within the first 30 seconds. | 2 |
| 14-15 | Poor | Very hard and difficult to disintegrate. Saliva increases but with many big non- dissolved particles though the first 30 sec. | 3 |
| 14-16 | Good | Nice crunchy fast dissolving tablet | 5 |
| 14-17 | Poor | Soft initial chew, different mouth feel. Sticky feeling. Does not dissolve fast enough or provide pleasant watering effect | 2 |
| 14-18 | Poor | Hard initial chew. Very crumble and sandy feeling. Salivation generation but sandy liquid feeling | 4 |

The above two-layer Ex14-13-14-18 were evaluated according to three parameters by a test panel.

Two of the parameters were suitability as a chewable tablet and one parameter was the perceived watering effect. Due to the more complex nature of a two-layer tablet, two further parameters were evaluated, namely resistance to crunch and friability.

It was first of all noted that the watering effect was considered relatively high for Ex14-13, 14-15, 14-16 and 14-18, i.e. the examples based on non-DC Xylitol, non-DC Isomalt, non-DC Erythritol and non-DC Maltitol. The watering effect is considered to be representative or equal to the elsewhere described salivation effect.

The test panel clearly indicated that the overall chewing process and the mouthfeel was no less than impressive in relation to Ex14-16 based on non-DC Erythritol. It was also noted that the test panel identified non-DC Xylitol of Ex14-13 and non-DC Maltitol of Ex14-18 as having an impressive watering effect when compared to e.g. the sorbitol-based example.

As a supplement to the sensory evaluation, the resistance to crunch and friability was measured and indicated in the Ex14-13-14-24, i.e. with reference to a bi-layer tablet with a first layer as indicated in Table 10 and Table 11 and a second layer based primarily on DC xylitol as indicated in Table 12.

The resistance to crunch is determined according to European Pharmacopoeia 9.1, test method 2.9.8. by using a pharmaceutical resistance to crunch tester model Pharma Test type PTB 311.

Friability is measured according to European Pharmacopoeia 9.1, test method 2.9.7. by using a pharmaceutical friability-tester PTF 10E from Pharma Test.

It is noted that the saliva generation from all non-DC sugar alcohols are impressive in the beginning, but it is also noted that saliva generation over time is no less than astonishing in relation to Ex14-16. It is thus noted that the salivation effect is increased a very long time after the major part of non-DC erythritol based tablet has been swallowed or collected during the measurement. It is also observed that the relatively low initial perceived salivation effect of Ex14-14, i.e. the sorbitol-based example is confirming the sensory evaluation as mentioned above.

Ex14-42-14-43. Preparation of Two-Layer Tablets with an ODT Tablet

TABLE 16

Oral tablet compositions for bi-layered tablets where the layer comprising Pearlitol Flash is an ODT layer.

| | Ex14-42 | Ex14-43 |
|---|---|---|
| Raw material (wt %) First layer | | |
| Non-DC Erythritol | 50 | 50 |
| DC Isomalt | — | 44.75 |
| Pearlitol Flash** | 44.75 | — |
| Flavor | 2 | 2 |
| HIS | 0.25 | 0.25 |
| Magnesium Stearate | 2 | 2 |
| Binder HPC | 1 | 1 |
| Raw material (wt %) Second layer | | |
| IE | 0.74 | 0.74 |
| Pearlitol Flash** | — | 97.06 |
| DC Xylitol | 97.06 | — |
| Flavor | 1 | 1 |
| HIS | 0.2 | 0.2 |
| Magnesium Stearate | 1 | 1 |

The ratio of layer 1 to layer 2 is 55:45. The tablet weight is 1.5 g. Hence the weight of layer 1 is 0.825 g whereas the weight of layer 2 is 0.675 g.

Amounts are given in wt-% of the respective layer of the tablet.

Pearlitol Flash** is a trademark of Roquette and is a compound that allies robustness with rapid disintegration and consists of mannitol and starch, specifically developed for disintegrating properties, melting instantaneously in the mouth into a creamy, slightly sweet texture.

IE = Ion-exchange composition particles.

TABLE 17

Oral tablet composition for bi-layered tablets where layer 2 is an ODT layer.

| | Ex14-43B |
|---|---|
| Raw material (wt %) First layer | |
| Non-DC Erythritol | 55 |
| DC Isomalt | 34.75 |
| Flavor | 4 |
| HIS | 0.25 |
| Magnesium Stearate | 1 |
| Binder HPC | 5 |
| Raw material (wt %) Second layer | |
| IE | 1.67 |
| DC Mannitol | 83.33 |
| Micro Crystalline Cellulose (MCC) | 5 |
| Binder CrosPovidone | 8 |
| Flavor | 1 |
| HIS | 1 |

The ratio of layer 1 to layer 2 is 75:25. The tablet weight is 1.2 g. Hence the weight of layer 1 is 0.90 g whereas the weight of layer 2 is 0.30 g.

Amounts are given in wt-% of the respective layer of the tablet.

The ODT layer was seen to disintegrate within 60 seconds.

IE = Ion-exchange composition particles.

Ex14-44-14-46 Preparation with Different Levels of Non-DC Sugar Alcohol

TABLE 18

Oral tablet compositions for bi-layered tablets.

| | Ex14-44 | Ex14-45 | Ex14-46 |
|---|---|---|---|
| Rw material (wt %) I layer | | | |
| Non-DC Erythritol | 5 | 50 | 82 |
| DC Isomalt | 90.8 | 43.8 | 9.8 |
| Flavor | 3 | 3 | 3 |
| HIS | 0.2 | 0.2 | 0.2 |
| Binder HPC | 1 | 3 | 5 |
| Raw material (wt %) Second layer | | | |
| IE | 0.74 | 0.74 | 0.74 |
| DC Xylitol | 91.16 | 91.16 | 91.16 |
| DC CaCO3 | 5 | 5 | 5 |
| Flavor | 3 | 3 | 3 |
| HIS | 0.1 | 0.1 | 0.1 |
| Resistance to crunch [N]* | 140 | 100 | 55 |
| Friability | 0.70 | 1.98 | 5.8 |

The ratio of layer 1 to layer 2 is 55:45. The tablet weight is 1.5 g. Hence the weight of layer 1 is 0.825 g whereas the weight of layer 2 is 0.675 g.

Amounts are given in wt-% of the respective layer of the tablet.

*Method limitation means maximum resistance to crunch which can be measured up to 350N.

IE = Ion-exchange composition particles.

Ex14-47-14-50 Preparation with Different Levels of Non-DC Sugar Alcohol

TABLE 19

Oral tablet compositions for bi-layered tablets.

| | Ex14-47 | Ex14-48 | Ex14-49 | Ex14-50 |
|---|---|---|---|---|
| Raw material (wt %) I layer | | | | |
| IE | 0.91 | 0.91 | 0.91 | 0.91 |
| DC Erythritol | 0 | 20 | 30 | 50 |
| Non-DC Erythritol | 50 | 30 | 20 | 0 |
| DC Isomalt | 42.89 | 42.89 | 42.89 | 42.89 |
| Flavor | 3 | 3 | 3 | 3 |
| HIS | 0.2 | 0.2 | 0.2 | 0.2 |
| Binder HPC | 3 | 3 | 3 | 3 |
| Raw material (wt %) Second layer | | | | |
| DC Xylitol | 91.9 | 91.9 | 91.9 | 91.9 |
| DC CaCO3 | 5 | 5 | 5 | 5 |
| Flavor | 3 | 3 | 3 | 3 |
| HIS | 0.1 | 0.1 | 0.1 | 0.1 |
| Resistance to crunch [N]* | 77 | 97 | 109 | 133 |
| Friability | 2.01 | 0.73 | 0.53 | 0.45 |

The ratio of layer 1 to layer 2 is 55:45. The tablet weight is 1.5 g. Hence the weight of layer 1 is 0.825 g whereas the weight of layer 2 is 0.675 g.

Amounts are given in wt-% of the respective layer of the tablet.

*Method limitation means maximum resistance to crunch which can be measured up to 350N.

IE = Ion-exchange composition particles.

Process Flow

The compositions indicated in the above Tables 16, 17, 18 and 19 are each processed into two-layer tablets with compositions as outlined in Ex14-42-14-50 and 14-43B.

For each Ex14-42-14-50 and 14-43B, the raw materials are sieved with a 1600-micron sieve and then weighed into the proper amount according to the exampled compositions.

The weighed amounts are then added to a Turbula mixer in a stainless-steel container and blended at 50 rpm for 5 minutes. If applicable, Magnesium stearate was added after 4 minutes of blending.

The mixtures are then tableted by means of a Piccola RIVA DC-SC-041-2 or a Fette 3090i.

The applied molds have circular cross sections with diameters of 16 mm and are hollowed to produce tablets, which are concave and/or curved. Evidently, other mold size and shapes may be applied within the scope of the invention.

The resulting tablets according to Ex14-42-14-50 and 43B are then obtained by tableting with a suitable pressure force.

For each tablet of Ex14-44-14-50, the second layer is pressed initially at a first relatively low pressure. The blended composition of the so-called first layer is then fed to the mold and a final two-layer tablet is then compressed at higher pressure than the pressure applied on the first layers, thereby producing final two-layer tablets according to Ex14-44-14-50. For Ex14-42-14-43 and 14-43B, the first layer is pressed initially at a first relatively low pressure. The blended composition of the so-called second layer is then fed to the mold and a final two-layer tablet is then compressed at higher pressure than the pressure applied on the first layers, thereby producing final two-layer tablets according to Ex14-42-14-43 and 14-43B.

It is noted that the final two-layer tablets of Ex14-42-14-43 are 1.5 grams tablets and the ratio of layer 1 to layer 2 is 55:45. The tablet weight is 1.5 g. Hence the weight of layer 1 is 0.825 g whereas the weight of layer 2 is 0.675 g.

It is noted that the final two-layer tablets of Ex14-43B are 1.2 grams tablets and the ratio of layer 1 to layer 2 is 75:25. The tablet weight is 1.2 g. Hence the weight of layer 1 is 0.90 g whereas the weight of layer 2 is 0.30 g.

It is noted that the final two-layer tablets of Ex14-44-14-50 are 1.5 grams tablets and the ratio of layer 1 to layer 2 is 55:45. The tablet weight is 1.5 g. Hence the weight of layer 1 is 0.825 g whereas the weight of layer 2 is 0.675 g.

A specification of relevant compounds applied in the examples explained above are listed below.

- HPC: Hydroxy propyl cellulose. Klucel Nutra D from Ashland
- Non-DC Xylitol: Xivia C from Dupont
- Non-granulated Sorbitol from PharmSorbidex from Cargill
- Non-DC Isomalt: Isomalt GS from Beneo Paltinit
- Non-DC Mannitol: Pearlitol from Roquette
- Non-DC Maltitol: Maltisorb. P200 from Roquette
- Non-DC Erythritol: Zerose 16952 from Cargill
- DC Erythritol—Zerose 16966 from Cargill
- DC Xylitol—Xylitab 200 from Dupont
- DC Isomalt—Isomalt DC 101 from Beneo Paltinit
- DC Mannitol—Pearlitol SD200 from Roquette
- DC Maltitol—Sweetpearl 300 DC from Roquette
- DC CaCO3: Scoralite 97 PVP from Scora
- Pearlitol Flash is a trademark from Roquette
- Micro Crystalline Cellulose (MCC): Avicel PH-105 from FMC
- CrosPovidone: Kollidon CL-SF from BASF

Example 15

Disintegration of Nicotine Tablets

The in vitro disintegration of the fast disintegrating tablets of FDT(a)-(f) and FDT(g)-(k) was carried out in accordance to European Pharmacopeia 9.0, section 2.9.1, *Disintegration of tablets and capsules*. As described in the examples each batch has been manufactured in various tablet sub lots where the compression force has been varied and therefore the output parameters like hardness and friability will also vary. These output parameters do also have an impact on in vitro disintegration. The results for FDT(a)-(f) are outlined in Table 20. A minimum and a maximum value for measured disintegration are given and this is more or less a function of the hardness.

TABLE 20

In vitro disintegration, hardness, friability.

| | Mean disintegration (sec) | | Mean hardness (N) | | Mean friability (%) | |
|---|---|---|---|---|---|---|
| | Min (sec) | Max (sec) | Min (N) | Max (N) | Min (%) | Max (%) |
| FDT(a) | 21 | 24 | 14 | 63 | 0.0 | 0.3 |
| FDT(b) | 23 | 98 | 12 | 50 | 0.0 | 0.6 |
| FDT(c) | 29 | 177 | 14 | 55 | 0.0 | 0.5 |
| FDT(d) | 15 | 177 | 19 | 62 | 0.0 | 0.0 |
| FDT(e) | 13 | 175 | 15 | 45 | 0.0 | 0.2 |
| FDT(f) | 11 | 259 | 14 | 43 | 0.0 | 0.2 |

Time is given in seconds.

When looking at e.g. FDT(a), the minimum mean disintegration time of 21 seconds correspond to a tablet pressed to have a minimum mean hardness of 14 N, and similarly the maximum mean disintegration time of 24 seconds correspond to another tablet pressed to have a maximum mean hardness of 63 N. In this way, the tablet having a mean friability of 0.3% of FDT(a) corresponds to the tablet having a mean hardness of 63 N. In other words, in table 4 FDT(a) refers to two different tablets pressed at two different pressures, the linking being indicated above.

The results for FDT(g)-(k) are outlined in Table 21.

TABLE 21

In vitro disintegration, hardness, friability.

| | Mean in vitro disintegration (sec) | | Mean hardness (N) | | Mean friability (%) | |
|---|---|---|---|---|---|---|
| | Min (sec) | Max (sec) | Min (N) | Max (N) | Min (%) | Max (%) |
| FDT(g) | 120 | 210 | 17 | 22 | N/A | 0.5 |
| FDT(h) | 40 | 80 | 16 | 24 | 0.5 | 0.8 |
| FDT(i) | 10 | 46 | 17 | 22 | 0.3 | 0.3 |
| FDT(j) | 42 | 150 | 17 | 22 | 0.7 | 1.0 |
| FDT(k) | 45 | 201 | 17 | 22 | 0.6 | 0.9 |

Time is given in seconds.

It is seen that the in vitro disintegrating may vary a lot between the disclosed fast disintegrating tablets. Hereby a disintegration profile as desired may be used together with a high in vivo pH, whereby the nicotine may be more efficiently used. Most preferable an in vitro disintegrating profile below 60 seconds is desired since it would ensure a high concentration of nicotine combined with relatively high in vivo pH.

The in vitro disintegration is a fast method to determine the time and mechanism for tablet performance. More preferable or in combination the in vivo disintegration is measured. The in vivo disintegration time is a value for the actual disintegration of the sublingual tablet under the tongue. Table 22 and 23 highlights the results for in vivo disintegration.

TABLE 22

In vivo disintegration.

| | Mean in vivo disintegration (sec) | |
|---|---|---|
| | Min (sec) | Max (sec) |
| FDT(a) | 34 | 52 |
| FDT(b) | 18 | 27 |
| FDT(c) | 37 | N/A |
| FDT(d) | 42 | N/A |
| FDT(e) | 46 | N/A |

Time is given in seconds.

TABLE 23

In vivo disintegration.

| | Mean in vivo disintegration (sec) | |
|---|---|---|
| | Min (sec) | Max (sec) |
| FDT(g) | 19 | 40 |
| FDT(h) | 13 | 48 |
| FDT(i) | 32 | 80 |
| FDT(j) | N/A | 56 |
| FDT(k) | N/A | 81 |

Time is given in seconds.

As recognized for the in vitro disintegration results above the speed of in vivo disintegrating may be varied between the disclosed batches. The disintegration time should be complete within 60 seconds from the onset of disintegration or preferable faster.

Example 16

Evaluation of the Oral Tablets with Respect to Burning, Bioavailability, Adherence to the Oral Mucosa and Stability In general, the experiments have revealed that the oral tablets with inclusion of the ion-exchange compositions result in less burning of the cationic biologically active compound, including nicotine, compared to conventional tablets. Also, the experiments have revealed that the tablets result in increased bioavailability of the cationic biologically active compound, including nicotine.

Furthermore, the experiments have revealed that the ion-exchange particles were particularly beneficial also for diminishing burning of nicotine and off notes associated with nicotine and for increasing bioavailability of nicotine. That the ion-exchange compositions were formulated into particles were particularly beneficial according to the invention. Critically, adherence of the particles to the oral mucosa upon use of the oral tablets were seen to take place to a considerable degree. Hence, the particles according to the invention in contact with the oral mucosa served to deliver nicotine for mucosal absorption and contributed significantly to increased bioavailability and taste masking of the cationic biologically active compound, such as nicotine.

Particularly beneficial results were revelated with respect to these effects with an average particle diameter of the particles of the water-soluble anionic mucoadhesive polymer loaded with a cationic biologically active compound, such as nicotine, in a certain range. The molecular weight of the water-soluble anionic polymer also did influence the properties with respect to both bioavailability and off notes. A combination of water-soluble anionic mucoadhesive polymers were particularly advantageous in some embodiments with respect to adherence to the oral mucosa.

FIG. 1 is an illustration of the properties of the particles of the water-soluble anionic mucoadhesive polymer according to the invention. Two series of experiments were conducted where particles of a water-soluble anionic mucoadhesive polymer were added to a petri dish containing 1 ml of aqua purificata. In experiment G(IPA), a powder according to Example 3 was applied. In experiment G, a powder according to Example 1 was applied. Pictures were taken initially (T0), after 5 minutes (T−5 min), after 10 minutes (T−10 min) and with additional water added after 10 minutes. The powder was precipitated in the water and was seen as blue discrete areas on the bottom of the petri dish. As a function of time, the blue colour gained more intensity. In particular, it was seen in experiment G that the discrete blue areas were more pronounced after 5 and 10 minutes. This indicates the principle of adhesion-by-hydration. Swelling occurred and the particles of the water-soluble anionic mucoadhesive polymer according to the invention gained in size.

FIG. 2 is an illustration of adherence to the oral mucosa according to the invention. A tablet made in accordance with Example 14-4 was administered to a subject, where the ion-exchange composition was exchanged with the particles of Example 1 having a blue color. After 5 minutes, the coloring was monitored for the subject. It can be seen that the blue color remaining on the oral mucosa, even after 5 minutes. This indicates the principle of adhesion-by-hydration. Swelling occurred and the particles of the water-soluble anionic mucoadhesive polymer according to the invention gained in size.

Finally, the stability of the oral tablets and the ion-exchange particles were seen to be comparable with conventional ion-exchange systems. A certain load of the cationic biologically active compound, including nicotine, were seen to further improve stability. The ratio of polymer: nicotine was seen to have an impact on the stability of the ion-exchange composition. Also, the ratio further had an effect on other properties, such as bioavailability and taste masking.

The invention claimed is:

1. An oral tablet for oromucosal delivery of biologically active compounds, the tablet comprising:

i) a sugar alcohol composition in powder form comprising one or more sugar alcohol particles selected from the group consisting of sorbitol particles, erythritol particles, xylitol particles, lactitol particles, maltitol particles, mannitol particles, isomalt particles, and combinations thereof, in an amount of at least 60% by weight of the tablet; and ii) an ion-exchange composition in powder form, the ion-exchange composition in powder form being located in the tablet as a separate composition mixed with the sugar alcohol composition in powder form, and the ion-exchange composition in powder form comprising a plurality of particles consisting of at least one water-soluble anionic mucoadhesive polymer loaded with nicotine, wherein an average particle diameter of the plurality of particles consisting essentially of the at least one water-soluble anionic mucoadhesive polymer loaded with nicotine is from 10 to 1000 microns, wherein the at least one water-soluble anionic mucoadhesive polymer is selected from sulfonated polysaccharides, anionic polysaccharides, polyacrylic acid, and combinations thereof, wherein the plurality of particles consisting of the at least one water-soluble anionic mucoadhesive polymer loaded with nicotine are operable to form a gel in contact with the oral mucosa when hydrated with saliva, wherein the plurality of particles consisting of the at least one water-soluble anionic mucoadhesive polymer loaded with nicotine are operable to protect the nicotine until adherence to the oral mucosa, wherein the weight ratio of the at least one water-soluble anionic mucoadhesive polymer to nicotine is from 2:1 to 20:1, and wherein the oral tablet is an orally disintegrating tablet.

2. The oral tablet according to claim 1, wherein a weight ratio of the at least one water-soluble anionic mucoadhesive polymer to nicotine is from 2:1 to 15:1.

3. The oral tablet according to claim 1, wherein the at least one water-soluble anionic mucoadhesive polymer is weakly acidic.

4. The oral tablet according to claim 1, wherein the at least one water-soluble anionic mucoadhesive polymer comprises carboxylic functional groups.

5. The oral tablet according to claim 1, wherein the at least one water-soluble anionic mucoadhesive polymer is selected from the group consisting of xanthan gum, carrageenan, carbomer, carboxymethyl cellulose and combinations thereof.

6. The oral tablet according to claim 1, wherein the oral tablet comprises the ion-exchange composition in an amount of 0.1 to 25% by weight of the tablet.

7. The oral tablet according to claim 1, wherein the oral tablet comprises a buffering agent in an amount of 1 to 5% by weight of the tablet.

8. The oral tablet according to claim 1, wherein the one or more sugar alcohol particles comprises non-DC sugar alcohol particles selected from non-DC particles of erythritol, maltitol, xylitol, isomalt, and combinations thereof.

9. The oral tablet according to claim 1, wherein the one or more sugar alcohol particles comprises at least 20% by weight of non-DC sugar alcohol particles with a particle size above 500 μm.

10. The oral tablet according to claim 1, wherein the one or more sugar alcohol particles comprises directly compressible (DC) and non-directly compressible (non-DC) sugar alcohol particles present in the tablet in a weight ratio between said non-DC sugar alcohol particles and said DC sugar alcohol particles of 0.2 and 1.2.

11. The oral tablet according to claim 1, wherein the one or more sugar alcohol particles is tableted into a first module and combined with a second population of particles that is tableted into a second module, and wherein the second module is different in composition than the first module.

12. The oral tablet according to claim 1, wherein the one or more sugar alcohol particles is tableted into a first module and combined with a second population of particles that is tableted into a second module, and wherein the second module includes gum base.

13. The oral tablet according to claim 1, wherein the oral tablet further comprises a disintegrant in an amount of 1 to 10% by weight of the tablet.

14. A powder composition comprising:

i) a sugar alcohol composition in powder form comprising one or more sugar alcohol particles selected from the group consisting of sorbitol particles, erythritol particles, xylitol particles, lactitol particles, maltitol particles, mannitol particles, isomalt particles, and combinations thereof, in an amount of at least 60% by weight of the powder composition; and ii) an ion-exchange composition in powder form for oromucosal delivery of biologically active compounds, the ion-exchange composition comprising:

a plurality of particles consisting of at least one water-soluble anionic mucoadhesive polymer loaded with nicotine, wherein an average particle diameter of the plurality of particles consisting of the at least one water-soluble anionic mucoadhesive polymer loaded with nicotine is from 10 to 1000 microns, wherein the at least one water-soluble anionic mucoadhesive polymer is selected from the group consisting of xanthan gum, carrageenan, carbomer, carboxymethyl cellulose and combinations thereof, wherein the plurality of particles consisting of the at least one water-soluble anionic mucoadhesive polymer loaded with nicotine are operable to form a gel in contact with the oral mucosa when hydrated with saliva, wherein the plurality of particles consisting of the at least one water-soluble anionic mucoadhesive polymer loaded with nicotine are operable to protect the biologically active compound until adherence to the oral mucosa, and wherein the weight ratio of the at least one water-soluble anionic mucoadhesive polymer to nicotine is from 2:1 to 20:1.

15. The powder composition according to claim 14, wherein the powder composition is included in a sachet.

16. The powder composition according to claim 14, wherein the ion-exchange composition ii) is made by providing a water slurry of the at least one water-soluble anionic mucoadhesive polymer, adding nicotine, and evaporating water from the slurry to obtain a final water content below 10% by weight of the ion exchange composition.

17. The powder composition according to claim 14, wherein the ion-exchange composition ii) is made by providing a water dispersion of the at least one water-soluble anionic mucoadhesive polymer, adding nicotine, and precipitating the composition from the dispersion by means of a suitable agent to obtain a final water content below 10% by weight of the ion exchange composition.

18. A powder composition comprising:

i) a sugar alcohol composition in powder form comprising one or more sugar alcohol particles selected from the group consisting of sorbitol particles, erythritol particles, xylitol particles, lactitol particles, maltitol particles, mannitol particles, isomalt particles, and combinations thereof, in an amount of at least 60% by weight of the powder composition; and ii) an ion-exchange composition in powder form for oromucosal delivery of nicotine, the ion-exchange composition comprising:

a plurality of particles consisting essentially of at least one polacrilex resin loaded with nicotine, the polacrilex resin loaded with nicotine being at least partly coated with at least one water-soluble anionic mucoadhesive polymer, wherein the at least one water-soluble anionic mucoadhesive polymer is selected from sulfonated polysaccharides, anionic polysaccharides, polyacrylic acid, and combinations thereof, wherein the at least one water-soluble anionic mucoadhesive polymer is operable to form a gel in contact with the oral mucosa when hydrated with saliva, wherein the at least one water-soluble anionic mucoadhesive polymer is operable to protect the nicotine until adherence to the oral mucosa, and wherein the weight ratio of the at least one water-soluble anionic mucoadhesive polymer to nicotine is from 2:1 to 20:1.

* * * * *